United States Patent [19]

Sloma et al.

[11] Patent Number: 5,621,089

[45] Date of Patent: Apr. 15, 1997

[54] NUCLEIC ACID CONSTRUCTS FOR THE PRODUCTION OF A BACILLUS ALKALINE PROTEASE

[75] Inventors: Alan P. Sloma, Davis, Calif.; Helle Outtrup, Ballerup, Denmark; Claus Dambmann, Søborg, Denmark; Dorrit A. Aaslyng, Roskilde, Denmark

[73] Assignees: Novo Nordisk Biotech, Inc., Davis, Calif.; Novo Nordisk A/S, Bagsvaerd, Denmark

[21] Appl. No.: 434,255

[22] Filed: May 3, 1995

Related U.S. Application Data

[63] Continuation-in-part of Ser. No. 325,386, filed as PCT/DK93/00183, May 26, 1993, Pat. No. 5,597,720.

[30] Foreign Application Priority Data

May 27, 1992 [DK] Denmark ................................. 702/92

[51] Int. Cl.$^6$ ........................... C12N 15/57; C12N 15/63; C12N 15/74; C12N 15/75
[52] U.S. Cl. ........................ 536/23.2; 536/23.7; 536/24.1; 435/69.1; 435/220; 435/221; 435/252.3; 435/252.31; 435/320.1; 935/14; 935/27; 935/29; 935/41; 935/66; 935/74
[58] Field of Search ..................................... 435/221, 222, 435/252.3, 252.31, 320.1; 536/23.2, 23.7

[56] References Cited

U.S. PATENT DOCUMENTS

| | | | |
|---|---|---|---|
| 4,480,037 | 10/1984 | Ichishima et al. | 435/221 |
| 4,559,300 | 12/1985 | Kovacevic et al. | 435/69.1 |
| 4,652,639 | 3/1987 | Stabinsky | 435/91.52 |
| 4,764,470 | 8/1988 | Durham et al. | 435/221 |
| 4,771,003 | 9/1988 | Stellwag et al. | 435/221 |
| 5,340,735 | 8/1994 | Christianson et al. | 435/221 |

FOREIGN PATENT DOCUMENTS

| | | |
|---|---|---|
| 0277260 | 7/1987 | European Pat. Off. . |
| 3328619 | 2/1985 | Germany . |
| WO92/17576 | 10/1992 | WIPO . |
| WO92/17577 | 10/1992 | WIPO . |
| WO92/17578 | 10/1992 | WIPO . |
| 93/24623 | 12/1993 | WIPO . |

OTHER PUBLICATIONS

Wells, J. A., et al., in The Genetics and Biotechnology of Bacilli, vol. 2, "Cloning and sequencing of a region controlling efficient expression of subtilisin from Bacillus amyloliquefaciens", pp. 173–180. 1983.

Wong, S.-L., et al., Proceedings of the National Academy of Sciences, U.S.A., vol. 81, "The subtilisin E gene of Bacillus subtilis is transcribed from a sigma37 promoter in vivo", pp. 1184–1188. 1984.

Jacobs, M., et al., Nucleic Acids Research, vol. 13, "Cloning, sequenceing and expression of subtilisin Carlsberg from Bacillus licheniformis", pp. 8913–8926. 1985.

Fortkamp, E., et al., DNA, vol. 5, "Cloning and expression in *Escherichia coli* of a synthetic DNA for hirudin, the blood coagulation inhibitor in the leech", pp. 511–517. 1986.

Maciver et al., Applied and Environmental Microbiology, vol. 60, No. 11 pp. 3981–3988 (1994).

*Primary Examiner*—Robert A. Wax
*Assistant Examiner*—William W. Moore
*Attorney, Agent, or Firm*—Steve T. Zelson, Esq.; Cheryl H. Agris, Esq.

[57] ABSTRACT

The invention is directed to an isolated nucleic acid construct(s) comprising a nucleic acid sequence encoding an alkaline protease having a molecular weight of about 34 kD and is obtainable from a strain of *Bacillus sp.* Group I, as well as recombinant vectors and host cells comprising such constructs. Additionally, the invention is directed to a method for obtaining the protease. The invention is also directed to promoter and signal sequences derived from said alkaline protease as well as methods of using the promoter and signal sequences in the expression of heterologous nucleic acid sequences encoding heterologous proteins in bacteria.

23 Claims, 19 Drawing Sheets

```
EcoRI
     ATG
  SO │
  ──┤ PRE │ PRO │        MATURE        │
     27 a.a.  90 a.a.         280 a.a.
```

```
EcoR 1    Mbo 1
  Mnl 1   Dpn 1          BspM 1              Mnl 1                      Bsm 1                 FnuH 1   Dde 1
  ....    :Taq 1         ....                ....                       ....                  ....    ....
GATTCTGAAGGGAGGATCGACCTGCTAATTTGTCTAAAAAATAGAAAATGAGGAATGCTTTATGAAGTTCAAAAAAATAGCCCGTCTATCCTTAG
                                                                        MetLysPheLysLysIleAlaAlaLeuSerLeu
                                                                       └──────────── PD498 ────────────
```

```
                              Ctr 1
                              Bal 1
                              Hae 1                                                HinP
                              Hae III                                              Hhr
              Mnl 1           Sec 1              Xmn 1                             H
  Spo 1       ....            Sty 1              ....                              ....
  ....                        ....
CAACTTCCCTGCTTATCCCTGCCTCCGAGGTAGTTCACTGGCCAAGGAAGCACCGAAACCGTTCCAACCTATCAACAAAACTTTGGATAAAGGCGC
AlaThrSerLeuAlaLeuPheProAlaPheGlyGlySerSerLeuAlaLysGluAlaProLysProPheGlnProIleAsnLysThrLeuAspLysGlyAla
                                     ──────────── PD498 ────────────
```

FIG. 3A

```
Asu 11
HinF 111
Taq 1
        HinF 1
        Hpa 11  Hph 1
.......  ......  .....
TTTCGAATCCGGTGAAGTCTCATCGTCAAATTCAAAGATGGTGTATCCAAAAAGGCCACAAGGTTCTGCTCTGAACAAAGCGGAGGCAAATGAACAGAAGCA
                                       |————————————————————— PD498 —————————————————————|
PheGluSerGlyGluValIleValLysPheLysAspGlyValSerLysLysAlaGlnGlyGlySerAlaLeuAsnLysAlaAsnGluAlaAsnGluGlnLysAla

MnI 1
                                                                         .....

StaN 1          Aha 11
Bin 1           Aha 11
Mbo 1           Mae 11   Aat 11
Xho 11          ......   Taq 1
                         Mbo 1
Dpn 1                    Dpn1 Alu1Mse1         HinF 111
.....                    ..........            ........
TCAGCAAAGATCCATTTCAGGTATTGGAAGTAGCGGACGTCGATCAAGCTGTTAAAGCACTGGAAAACAATCCGAATGTAGAATATGCTGAACCAAACT
                                   |———————————————————————— PD498 ————————————————————————|
SerAlaLysAspProPheGlnValLeuGluValAlaAspValAlaAspGlnAlaValLysAlaLeuGluAsnAsnProAsnValGluTyrAlaGluProAsn
```

FIG. 3B

```
                    Sec 1                     Sal 1
                    Sty 1                     Acc 1           Ava 111        Bbv 1         Ec15
                    Mnl1 HinF111 Bsm 1  Afl11 Taq 1           Nsi 1          Alu 1         FnuH 1
        Rsa 1       ......  .....        Mse 1   Hinc 11     Nla 111        Bbv 1         Fnu 1
        ......                            ......   ......      ......         ......        ......

AAAGGTACTCAACTCTCCCTTGGTTGCCAATGCAACTCCACAACTCTTAAGAGTCGTCCGTCGACTATGCATGGAACAACAAGGAGCTGTAGTCGTTGCTGCT
                                                            ————————— PD498 —————————

LysValLeuAsnLeuSerLeuGlyCysGluCysAsnSerThrThrLeuLysSerAlaValAspTyrAlaAlaTrpAsnLysGlyAlaValValAlaAla

HgiC 1             Mbo 1
                                                      Nla IV             Dpn 1
              Pst 1         Rsa 1           Alu 1     Ple 1 HinF 1       Taq 1
              ......        ......          ......   ......  ......     ......

GCAGGGAATGACAATGTATCCGTACATTCCAACCAGCTTCTTACCCTAATGCCATTGCAGTAGGTGCCATTGACTCCAATGATCGAAAAGCATCATTCT
                                                ————————— PD498 —————————

AlaGlyAsnAspAsnValSerArgThrPheGlnProAlaSerTyrProAsnAlaIleAlaValGlyAlaIleAspSerAsnAspArgLysAlaSerPhe

FIG. 3E
```

```
                                                                    Nco 1
                                                             Mae II  Sec 1
                                                       Rsa 1         Sty1
                                      Afl III          ...........
                                      Nla III
                                      NspH 1
                                      Fok 1
                     StaN 1
                     HinF III
              Spo
EcoR II
Fok 1
Apy 1
Mae II    Mae III    SerF 1

CCAATTACGGAACGTGGGTGGATGTCACTGCTCCAGGTGTGAACATAACCGTTCCGAATAATGGCTACTCCTACATGTCTGGTACGTCCATGGC
|————————————————————————————————————— PD498 ———————————————————————————————————————|

SerAsnTyrGlyThrTrpValAspValThrAlaProGlyValAsnIleAlaSerThrValProAsnAsnGlyTyrSerTyrMetSerGlyThrSerMetAla
```

ATCCCCCTCACGTGGCCGGTTTGGCTGCTTTGTTGGCAAGTCAAGGTAAGAATAACGTACAAATCCGCCAGGCCATTGAGCAAACCCGCGATAAGATCTCT

SerProHisValAlaGlyLeuAlaAlaLeuLeuAlaSerGlnGlyLysAsnAsnValGlnIleArgGlnAlaIleGluGlnThrAlaAspLysIleSer
————————————————PD498————————————————

GGCACTGGAACAAACTTCAAGTATGTAAAATCAACTCAAACAAGCTGTAAGATACTAATAGATAAACAAGAGCACCCGTGAATGGTGGGCTCTTTC

GlyThrGlyThrAsnPheLysTyrGlyLysIleAsnSerAsnLysAlaValArgTyr
————————————————PD498————————————————

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 2702 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 843..2033

( x i ) SEQUENCE DESCRIPTION: SEQ ID NO:1:

| | | | | |
|---|---|---|---|---|
| AAGCTTAATC | ATCCCGATGT | ATCGCTTCAG | CGCTTACCGT AGACGATTTT | CTTTATAGTC | 60 |
| TCGATGGATA | AAAAGTACCT | ATCTGAAATG | GAAGCAATCG ACTCTCCTCC | AGTAAAGGCT | 120 |
| TCAAGGATCG | ACGTGTTTCT | CCGTTTAAGC | GCTTCCCTTC CTCCTGACTT | TGAGCCCCAG | 180 |
| GCATTATACT | CTTCTTTTCG | CTTTGGGATA | TAAATGGTTT GGCCTTGAAC | ATAGTTTTGT | 240 |
| AATTCTCTCA | TTAAGTAATC | AGGAATTTGA | TTTACTGCTT TCAATCGTGT | CAGCTCCTTA | 300 |
| TCATTATTGG | ATCAATAAGG | GACAAAGCCG | ACATATGAAT GGCGATTCAT | CTAAAACTAC | 360 |
| CACCCCATGC | AAAGGATCGC | CGAATCATAC | AGGCTTTGCA TGAGATGCTG | CAGATTTCGG | 420 |
| AAAACGGATT | TCCATATGAT | CACCTCCTAG | TATCAGTATA CTGATACTAG | CAGAAAGATT | 480 |
| TCCATAAGAA | TTTCTTATAG | TTACCATAAT | ATTATTATAT AAACCTACTA | TATTTGATTT | 540 |
| TCAATTTGAG | AAAATAAGTG | ACCATTCACC | TATCCTTAAA GTTGCTCAAC | CCCATACAAT | 600 |
| CATGAAACTT | TTCATGCCAA | ACGTTCATTA | TGCGAAATCT ATCAAAAACT | GAGAGTGAAT | 660 |
| TCATTTTTTG | ATAGAAAATT | AAAACTATTC | AATATTTTGT CACAACCTGC | TAGAATCCTA | 720 |
| GGTAATAAGG | GTCCCTACA | TATCTATCAT | TCATCACAAT GACCTTTGTT | CATCTTGAAT | 780 |
| TCTGAAGGGA | GGATCGACCT | GCTAATTTGT | CGTAAAAAAA TAGAAAATGG | AGGAATGCTT | 840 |

```
TT ATG AAG TTC AAA AAA ATA GCC GCT CTA TCC TTA GCA ACT TCC CTT                887
   Met Lys Phe Lys Lys Ile Ala Ala Leu Ser Leu Ala Thr Ser Leu
   1               5                  10                  15

GCT TTA TTC CCT GCC TTC GGA GGT AGT TCA CTG GCC AAG GAA GCA CCG                935
Ala Leu Phe Pro Ala Phe Gly Gly Ser Ser Leu Ala Lys Glu Ala Pro
                20                  25                  30

AAA CCG TTC CAA CCT ATC AAC AAA ACT TTG GAT AAA GGC GCT TTC GAA                983
Lys Pro Phe Gln Pro Ile Asn Lys Thr Leu Asp Lys Gly Ala Phe Glu
                35                  40                  45

TCC GGT GAA GTC ATC GTC AAA TTC AAA GAT GGT GTA TCC AAA AAG GCA               1031
Ser Gly Glu Val Ile Val Lys Phe Lys Asp Gly Val Ser Lys Lys Ala
            50                  55                  60

CAA GGT TCT GCT CTG AAC AAA GCG GAG GCA AAT GAA CAG AAA GCA TCA               1079
Gln Gly Ser Ala Leu Asn Lys Ala Glu Ala Asn Glu Gln Lys Ala Ser
        65                  70                  75

GCA AAA GAT CCA TTT CAG GTA TTG GAA GTA GCG GAC GTC GAT CAA GCT               1127
Ala Lys Asp Pro Phe Gln Val Leu Glu Val Ala Asp Val Asp Gln Ala
80                  85                  90                  95

GTT AAA GCA CTG GAA AAC AAT CCG AAT GTA GAA TAT GCT GAA CCA AAC               1175
Val Lys Ala Leu Glu Asn Asn Pro Asn Val Glu Tyr Ala Glu Pro Asn
                100                 105                 110

TAT ACC TTC CAA GCG ACT TGG TCA CCG AAT GAC CCT TAC TAT TCT GCT               1223
Tyr Thr Phe Gln Ala Thr Trp Ser Pro Asn Asp Pro Tyr Tyr Ser Ala
                115                 120                 125

TAC CAG TAT GGA CCA CAA AAC ACC TCA ACC CCT GCT GCC TGG GAT GTA               1271
Tyr Gln Tyr Gly Pro Gln Asn Thr Ser Thr Pro Ala Ala Trp Asp Val
            130                 135                 140

ACC CGT GGA AGC AGC ACT CAA ACG GTG GCG GTC CTT GAT TCC GGA GTG               1319
Thr Arg Gly Ser Ser Thr Gln Thr Val Ala Val Leu Asp Ser Gly Val
        145                 150                 155

GAT TAT AAC CAC CCT GAT CTT GCA AGA AAA GTA ATA AAA GGG TAC GAC               1367
Asp Tyr Asn His Pro Asp Leu Ala Arg Lys Val Ile Lys Gly Tyr Asp
160                 165                 170                 175

TTT ATC GAC AGG GAC AAT AAC CCA ATG GAT CTT AAC GGA CAT GGT ACC               1415
Phe Ile Asp Arg Asp Asn Asn Pro Met Asp Leu Asn Gly His Gly Thr
                180                 185                 190

CAT GTT GCC GGT ACT GTT GCT GCT GAT ACG AAC AAT GGA ATT GGC GTA               1463
His Val Ala Gly Thr Val Ala Ala Asp Thr Asn Asn Gly Ile Gly Val
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 195 |     |     |     |     | 200 |     |     |     |     | 205 |     |      |
| GCC | GGT | ATG | GCA | CCA | GAT | ACG | AAG | ATC | CTT | GCC | GTA | CGG | GTC | CTT | GAT | 1511 |
| Ala | Gly | Met | Ala | Pro | Asp | Thr | Lys | Ile | Leu | Ala | Val | Arg | Val | Leu | Asp |      |
|     |     | 210 |     |     |     |     | 215 |     |     |     |     | 220 |     |     |     |      |
| GCC | AAT | GGA | AGT | GGC | TCA | CTT | GAC | AGC | ATT | GCC | TCA | GGT | ATC | CGC | TAT | 1559 |
| Ala | Asn | Gly | Ser | Gly | Ser | Leu | Asp | Ser | Ile | Ala | Ser | Gly | Ile | Arg | Tyr |      |
|     | 225 |     |     |     |     | 230 |     |     |     |     | 235 |     |     |     |     |      |
| GCT | GCT | GAT | CAA | GGG | GCA | AAG | GTA | CTC | AAC | CTC | TCC | CTT | GGT | TGC | GAA | 1607 |
| Ala | Ala | Asp | Gln | Gly | Ala | Lys | Val | Leu | Asn | Leu | Ser | Leu | Gly | Cys | Glu |      |
| 240 |     |     |     | 245 |     |     |     |     | 250 |     |     |     |     | 255 |     |      |
| TGC | AAC | TCC | ACA | ACT | CTT | AAG | AGT | GCC | GTC | GAC | TAT | GCA | TGG | AAC | AAA | 1655 |
| Cys | Asn | Ser | Thr | Thr | Leu | Lys | Ser | Ala | Val | Asp | Tyr | Ala | Trp | Asn | Lys |      |
|     |     |     | 260 |     |     |     |     | 265 |     |     |     |     | 270 |     |     |      |
| GGA | GCT | GTA | GTC | GTT | GCT | GCT | GCA | GGG | AAT | GAC | AAT | GTA | TCC | CGT | ACA | 1703 |
| Gly | Ala | Val | Val | Val | Ala | Ala | Ala | Gly | Asn | Asp | Asn | Val | Ser | Arg | Thr |      |
|     |     |     | 275 |     |     |     |     | 280 |     |     |     |     | 285 |     |     |      |
| TTC | CAA | CCA | GCT | TCT | TAC | CCT | AAT | GCC | ATT | GCA | GTA | GGT | GCC | ATT | GAC | 1751 |
| Phe | Gln | Pro | Ala | Ser | Tyr | Pro | Asn | Ala | Ile | Ala | Val | Gly | Ala | Ile | Asp |      |
|     |     | 290 |     |     |     |     | 295 |     |     |     |     | 300 |     |     |     |      |
| TCC | AAT | GAT | CGA | AAA | GCA | TCA | TTC | TCC | AAT | TAC | GGA | ACG | TGG | GTG | GAT | 1799 |
| Ser | Asn | Asp | Arg | Lys | Ala | Ser | Phe | Ser | Asn | Tyr | Gly | Thr | Trp | Val | Asp |      |
|     | 305 |     |     |     |     | 310 |     |     |     |     | 315 |     |     |     |     |      |
| GTC | ACT | GCT | CCA | GGT | GTG | AAC | ATA | GCA | TCA | ACC | GTT | CCG | AAT | AAT | GGC | 1847 |
| Val | Thr | Ala | Pro | Gly | Val | Asn | Ile | Ala | Ser | Thr | Val | Pro | Asn | Asn | Gly |      |
| 320 |     |     |     |     | 325 |     |     |     |     | 330 |     |     |     |     | 335 |      |
| TAC | TCC | TAC | ATG | TCT | GGT | ACG | TCC | ATG | GCA | TCC | CCT | CAC | GTG | GCC | GGT | 1895 |
| Tyr | Ser | Tyr | Met | Ser | Gly | Thr | Ser | Met | Ala | Ser | Pro | His | Val | Ala | Gly |      |
|     |     |     |     | 340 |     |     |     |     | 345 |     |     |     |     | 350 |     |      |
| TTG | GCT | GCT | TTG | TTG | GCA | AGT | CAA | GGT | AAG | AAT | AAC | GTA | CAA | ATC | CGC | 1943 |
| Leu | Ala | Ala | Leu | Leu | Ala | Ser | Gln | Gly | Lys | Asn | Asn | Val | Gln | Ile | Arg |      |
|     |     |     | 355 |     |     |     |     | 360 |     |     |     |     | 365 |     |     |      |
| CAG | GCC | ATT | GAG | CAA | ACC | GCC | GAT | AAG | ATC | TCT | GGC | ACT | GGA | ACA | AAC | 1991 |
| Gln | Ala | Ile | Glu | Gln | Thr | Ala | Asp | Lys | Ile | Ser | Gly | Thr | Gly | Thr | Asn |      |
|     |     | 370 |     |     |     |     | 375 |     |     |     |     | 380 |     |     |     |      |
| TTC | AAG | TAT | GGT | AAA | ATC | AAC | TCA | AAC | AAA | GCT | GTA | AGA | TAC |     |     | 2033 |
| Phe | Lys | Tyr | Gly | Lys | Ile | Asn | Ser | Asn | Lys | Ala | Val | Arg | Tyr |     |     |      |
|     | 385 |     |     |     |     | 390 |     |     |     |     | 395 |     |     |     |     |      |

| | | | | |
|---|---|---|---|---|
| TAATAGATAA | AACAAGAGCA | CACCGTGAAT | GGTGGGCTCT | TTCATTATGT | TCACTACTGT | 2093 |
| TTTACGATCT | GGCCGTTTTG | GTTCAGGTAA | ACACTCTGGA | TGATGGTTCT | ATTAAACGGT | 2153 |
| TTCCCTTTAT | AATCAGACTT | AATATCCGTT | GTCAGGTTGT | AGGTTCCTTC | TCCTCCATTG | 2213 |
| AACACTGTAC | CACTCCCCTT | GACAGACTGG | GACAAAGGTT | TCCCCTTAGG | GTAGAACTCA | 2273 |
| AACATTGTGT | GCTCGGTGAA | CCCACTGACG | ATACTTGATT | GAACGCTGAC | TCCCTTCTCA | 2333 |
| GTGGTCGTTA | CCACCAAGTC | ATCATTCAAT | GGACTTGTGA | AACCAACATT | CAGTAAATAT | 2393 |
| GCCCCAGGTT | CTTTTGACAA | AGATGACACC | TTCCACTCGC | CTTCAATAGG | GTTTTCAACC | 2453 |
| GTTCCCACAT | GATGAAACGC | ACCTTTGAAA | TAACTTTCCT | GATCCTTTCC | AGATGGTTTC | 2513 |
| AGTGCCGTTA | CCTTCCCATC | TGGGCTTGTA | AGGTAGACAT | CTTCCTTCGA | GTTCGATGCC | 2573 |
| AACCAGTCAA | TCGAAATCCG | TTCTGCCCCA | ACCTCTACCC | AGAAAGTTTC | ATCCGCATGC | 2633 |
| TCTTTATACT | CACCTCCGCG | GATGAAGGAT | GAAGTATTGG | TCTTGAGAGC | CGATTCCTTC | 2693 |
| CTTGATATC | | | | | | 2702 |

( 2 ) INFORMATION FOR SEQ ID NO:2:

( i ) SEQUENCE CHARACTERISTICS:
( A ) LENGTH: 397 amino acids
( B ) TYPE: amino acid (D) TOPOLOGY: linear (ii) MOLECULE TYPE: protein (xi) SEQUENCE DESCRIPTION: SEQ ID NO:2:

```
Met Lys Phe Lys Lys Ile Ala Ala Leu Ser Leu Ala Thr Ser Leu Ala
 1               5                  10                  15

Leu Phe Pro Ala Phe Gly Gly Ser Ser Leu Ala Lys Glu Ala Pro Lys
            20                  25                  30

Pro Phe Gln Pro Ile Asn Lys Thr Leu Asp Lys Gly Ala Phe Glu Ser
        35                  40                  45

Gly Glu Val Ile Val Lys Phe Lys Asp Gly Val Ser Lys Lys Ala Gln
    50                  55                  60

Gly Ser Ala Leu Asn Lys Ala Glu Ala Asn Glu Gln Lys Ala Ser Ala
65                  70                  75                  80

Lys Asp Pro Phe Gln Val Leu Glu Val Ala Asp Val Asp Gln Ala Val
                85                  90                  95

Lys Ala Leu Glu Asn Asn Pro Asn Val Glu Tyr Ala Glu Pro Asn Tyr
            100                 105                 110

Thr Phe Gln Ala Thr Trp Ser Pro Asn Asp Pro Tyr Tyr Ser Ala Tyr
        115                 120                 125

Gln Tyr Gly Pro Gln Asn Thr Ser Thr Pro Ala Ala Trp Asp Val Thr
    130                 135                 140

Arg Gly Ser Ser Thr Gln Thr Val Ala Val Leu Asp Ser Gly Val Asp
145                 150                 155                 160

Tyr Asn His Pro Asp Leu Ala Arg Lys Val Ile Lys Gly Tyr Asp Phe
                165                 170                 175

Ile Asp Arg Asp Asn Asn Pro Met Asp Leu Asn Gly His Gly Thr His
            180                 185                 190

Val Ala Gly Thr Val Ala Ala Asp Thr Asn Asn Gly Ile Gly Val Ala
        195                 200                 205

Gly Met Ala Pro Asp Thr Lys Ile Leu Ala Val Arg Val Leu Asp Ala
    210                 215                 220

Asn Gly Ser Gly Ser Leu Asp Ser Ile Ala Ser Gly Ile Arg Tyr Ala
225                 230                 235                 240

Ala Asp Gln Gly Ala Lys Val Leu Asn Leu Ser Leu Gly Cys Glu Cys
                245                 250                 255

Asn Ser Thr Thr Leu Lys Ser Ala Val Asp Tyr Ala Trp Asn Lys Gly
            260                 265                 270

Ala Val Val Val Ala Ala Ala Gly Asn Asp Asn Val Ser Arg Thr Phe
        275                 280                 285

Gln Pro Ala Ser Tyr Pro Asn Ala Ile Ala Val Gly Ala Ile Asp Ser
    290                 295                 300

Asn Asp Arg Lys Ala Ser Phe Ser Asn Tyr Gly Thr Trp Val Asp Val
305                 310                 315                 320

Thr Ala Pro Gly Val Asn Ile Ala Ser Thr Val Pro Asn Asn Gly Tyr
                325                 330                 335

Ser Tyr Met Ser Gly Thr Ser Met Ala Ser Pro His Val Ala Gly Leu
            340                 345                 350

Ala Ala Leu Leu Ala Ser Gln Gly Lys Asn Asn Val Gln Ile Arg Gln
        355                 360                 365

Ala Ile Glu Gln Thr Ala Asp Lys Ile Ser Gly Thr Gly Thr Asn Phe
    370                 375                 380

Lys Tyr Gly Lys Ile Asn Ser Asn Lys Ala Val Arg Tyr
385                 390                 395
```

( 2 ) INFORMATION FOR SEQ ID NO:3:

( i ) SEQUENCE CHARACTERISTICS:
        ( A ) LENGTH: 1191 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..1191

( x i ) SEQUENCE DESCRIPTION: SEQ ID NO:3:

```
ATG AAG TTC AAA AAA ATA GCC GCT CTA TCC TTA GCA ACT TCC CTT GCT      48
Met Lys Phe Lys Lys Ile Ala Ala Leu Ser Leu Ala Thr Ser Leu Ala
        400             405             410

TTA TTC CCT GCC TTC GGA GGT AGT TCA CTG GCC AAG GAA GCA CCG AAA      96
Leu Phe Pro Ala Phe Gly Gly Ser Ser Leu Ala Lys Glu Ala Pro Lys
    415             420             425

CCG TTC CAA CCT ATC AAC AAA ACT TTG GAT AAA GGC GCT TTC GAA TCC     144
Pro Phe Gln Pro Ile Asn Lys Thr Leu Asp Lys Gly Ala Phe Glu Ser
430             435             440             445

GGT GAA GTC ATC GTC AAA TTC AAA GAT GGT GTA TCC AAA AAG GCA CAA     192
Gly Glu Val Ile Val Lys Phe Lys Asp Gly Val Ser Lys Lys Ala Gln
                450             455             460

GGT TCT GCT CTG AAC AAA GCG GAG GCA AAT GAA CAG AAA GCA TCA GCA     240
Gly Ser Ala Leu Asn Lys Ala Glu Ala Asn Glu Gln Lys Ala Ser Ala
            465             470             475

AAA GAT CCA TTT CAG GTA TTG GAA GTA GCG GAC GTC GAT CAA GCT GTT     288
Lys Asp Pro Phe Gln Val Leu Glu Val Ala Asp Val Asp Gln Ala Val
        480             485             490

AAA GCA CTG GAA AAC AAT CCG AAT GTA GAA TAT GCT GAA CCA AAC TAT     336
Lys Ala Leu Glu Asn Asn Pro Asn Val Glu Tyr Ala Glu Pro Asn Tyr
    495             500             505

ACC TTC CAA GCG ACT TGG TCA CCG AAT GAC CCT TAC TAT TCT GCT TAC     384
Thr Phe Gln Ala Thr Trp Ser Pro Asn Asp Pro Tyr Tyr Ser Ala Tyr
510             515             520             525

CAG TAT GGA CCA CAA AAC ACC TCA ACC CCT GCT GCC TGG GAT GTA ACC     432
Gln Tyr Gly Pro Gln Asn Thr Ser Thr Pro Ala Ala Trp Asp Val Thr
                530             535             540

CGT GGA AGC AGC ACT CAA ACG GTG GCG GTC CTT GAT TCC GGA GTG GAT     480
Arg Gly Ser Ser Thr Gln Thr Val Ala Val Leu Asp Ser Gly Val Asp
            545             550             555

TAT AAC CAC CCT GAT CTT GCA AGA AAA GTA ATA AAA GGG TAC GAC TTT     528
Tyr Asn His Pro Asp Leu Ala Arg Lys Val Ile Lys Gly Tyr Asp Phe
        560             565             570

ATC GAC AGG GAC AAT AAC CCA ATG GAT CTT AAC GGA CAT GGT ACC CAT     576
Ile Asp Arg Asp Asn Asn Pro Met Asp Leu Asn Gly His Gly Thr His
    575             580             585

GTT GCC GGT ACT GTT GCT GCT GAT ACG AAC AAT GGA ATT GGC GTA GCC     624
Val Ala Gly Thr Val Ala Ala Asp Thr Asn Asn Gly Ile Gly Val Ala
590             595             600             605

GGT ATG GCA CCA GAT ACG AAG ATC CTT GCC GTA CGG GTC CTT GAT GCC     672
Gly Met Ala Pro Asp Thr Lys Ile Leu Ala Val Arg Val Leu Asp Ala
                610             615             620

AAT GGA AGT GGC TCA CTT GAC AGC ATT GCC TCA GGT ATC CGC TAT GCT     720
Asn Gly Ser Gly Ser Leu Asp Ser Ile Ala Ser Gly Ile Arg Tyr Ala
            625             630             635

GCT GAT CAA GGG GCA AAG GTA CTC AAC CTC TCC CTT GGT TGC GAA TGC     768
Ala Asp Gln Gly Ala Lys Val Leu Asn Leu Ser Leu Gly Cys Glu Cys
        640             645             650
```

| | | | | | | | | | | | | | | | | |
|---|---|---|---|---|---|---|---|---|---|---|---|---|---|---|---|---|
| AAC | TCC | ACA | ACT | CTT | AAG | AGT | GCC | GTC | GAC | TAT | GCA | TGG | AAC | AAA | GGA | 816 |
| Asn | Ser | Thr | Thr | Leu | Lys | Ser | Ala | Val | Asp | Tyr | Ala | Trp | Asn | Lys | Gly | |
| | 655 | | | | 660 | | | | | 665 | | | | | | |
| GCT | GTA | GTC | GTT | GCT | GCT | GCA | GGG | AAT | GAC | AAT | GTA | TCC | CGT | ACA | TTC | 864 |
| Ala | Val | Val | Val | Ala | Ala | Ala | Gly | Asn | Asp | Asn | Val | Ser | Arg | Thr | Phe | |
| 670 | | | | | 675 | | | | | 680 | | | | | 685 | |
| CAA | CCA | GCT | TCT | TAC | CCT | AAT | GCC | ATT | GCA | GTA | GGT | GCC | ATT | GAC | TCC | 912 |
| Gln | Pro | Ala | Ser | Tyr | Pro | Asn | Ala | Ile | Ala | Val | Gly | Ala | Ile | Asp | Ser | |
| | | | | 690 | | | | | 695 | | | | | 700 | | |
| AAT | GAT | CGA | AAA | GCA | TCA | TTC | TCC | AAT | TAC | GGA | ACG | TGG | GTG | GAT | GTC | 960 |
| Asn | Asp | Arg | Lys | Ala | Ser | Phe | Ser | Asn | Tyr | Gly | Thr | Trp | Val | Asp | Val | |
| | | | 705 | | | | | 710 | | | | | 715 | | | |
| ACT | GCT | CCA | GGT | GTG | AAC | ATA | GCA | TCA | ACC | GTT | CCG | AAT | AAT | GGC | TAC | 1008 |
| Thr | Ala | Pro | Gly | Val | Asn | Ile | Ala | Ser | Thr | Val | Pro | Asn | Asn | Gly | Tyr | |
| | | 720 | | | | | 725 | | | | | 730 | | | | |
| TCC | TAC | ATG | TCT | GGT | ACG | TCC | ATG | GCA | TCC | CCT | CAC | GTG | GCC | GGT | TTG | 1056 |
| Ser | Tyr | Met | Ser | Gly | Thr | Ser | Met | Ala | Ser | Pro | His | Val | Ala | Gly | Leu | |
| | 735 | | | | | 740 | | | | | 745 | | | | | |
| GCT | GCT | TTG | TTG | GCA | AGT | CAA | GGT | AAG | AAT | AAC | GTA | CAA | ATC | CGC | CAG | 1104 |
| Ala | Ala | Leu | Leu | Ala | Ser | Gln | Gly | Lys | Asn | Asn | Val | Gln | Ile | Arg | Gln | |
| 750 | | | | | 755 | | | | | 760 | | | | | 765 | |
| GCC | ATT | GAG | CAA | ACC | GCC | GAT | AAG | ATC | TCT | GGC | ACT | GGA | ACA | AAC | TTC | 1152 |
| Ala | Ile | Glu | Gln | Thr | Ala | Asp | Lys | Ile | Ser | Gly | Thr | Gly | Thr | Asn | Phe | |
| | | | | 770 | | | | | 775 | | | | | 780 | | |
| AAG | TAT | GGT | AAA | ATC | AAC | TCA | AAC | AAA | GCT | GTA | AGA | TAC | | | | 1191 |
| Lys | Tyr | Gly | Lys | Ile | Asn | Ser | Asn | Lys | Ala | Val | Arg | Tyr | | | | |
| | | | 785 | | | | | 790 | | | | | | | | |

( 2 ) INFORMATION FOR SEQ ID NO:4:

( i ) SEQUENCE CHARACTERISTICS:
        ( A ) LENGTH: 397 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | | |
|---|---|---|---|---|---|---|---|---|---|---|---|---|---|---|---|
| Met | Lys | Phe | Lys | Lys | Ile | Ala | Ala | Leu | Ser | Leu | Ala | Thr | Ser | Leu | Ala |
| 1 | | | | 5 | | | | | 10 | | | | | 15 | |
| Leu | Phe | Pro | Ala | Phe | Gly | Gly | Ser | Ser | Leu | Ala | Lys | Glu | Ala | Pro | Lys |
| | | | 20 | | | | | 25 | | | | | 30 | | |
| Pro | Phe | Gln | Pro | Ile | Asn | Lys | Thr | Leu | Asp | Lys | Gly | Ala | Phe | Glu | Ser |
| | | | 35 | | | | 40 | | | | | 45 | | | |
| Gly | Glu | Val | Ile | Val | Lys | Phe | Lys | Asp | Gly | Val | Ser | Lys | Lys | Ala | Gln |
| | 50 | | | | | 55 | | | | | 60 | | | | |
| Gly | Ser | Ala | Leu | Asn | Lys | Ala | Glu | Ala | Asn | Glu | Gln | Lys | Ala | Ser | Ala |
| 65 | | | | | 70 | | | | | 75 | | | | | 80 |
| Lys | Asp | Pro | Phe | Gln | Val | Leu | Glu | Val | Ala | Asp | Val | Asp | Gln | Ala | Val |
| | | | | 85 | | | | | 90 | | | | | 95 | |
| Lys | Ala | Leu | Glu | Asn | Asn | Pro | Asn | Val | Glu | Tyr | Ala | Glu | Pro | Asn | Tyr |
| | | | 100 | | | | | 105 | | | | | 110 | | |
| Thr | Phe | Gln | Ala | Thr | Trp | Ser | Pro | Asn | Asp | Pro | Tyr | Tyr | Ser | Ala | Tyr |
| | | | 115 | | | | | 120 | | | | | 125 | | |
| Gln | Tyr | Gly | Pro | Gln | Asn | Thr | Ser | Thr | Pro | Ala | Ala | Trp | Asp | Val | Thr |
| | | 130 | | | | | 135 | | | | | 140 | | | |
| Arg | Gly | Ser | Ser | Thr | Gln | Thr | Val | Ala | Val | Leu | Asp | Ser | Gly | Val | Asp |
| 145 | | | | | 150 | | | | | 155 | | | | | 160 |
| Tyr | Asn | His | Pro | Asp | Leu | Ala | Arg | Lys | Val | Ile | Lys | Gly | Tyr | Asp | Phe |
| | | | | 165 | | | | | 170 | | | | | 175 | |

```
Ile  Asp  Arg  Asp  Asn  Asn  Pro  Met  Asp  Leu  Asn  Gly  His  Gly  Thr  His
          180                      185                      190

Val  Ala  Gly  Thr  Val  Ala  Ala  Asp  Thr  Asn  Asn  Gly  Ile  Gly  Val  Ala
          195                      200                      205

Gly  Met  Ala  Pro  Asp  Thr  Lys  Ile  Leu  Ala  Val  Arg  Val  Leu  Asp  Ala
     210                      215                      220

Asn  Gly  Ser  Gly  Ser  Leu  Asp  Ser  Ile  Ala  Ser  Gly  Ile  Arg  Tyr  Ala
225                           230                      235                      240

Ala  Asp  Gln  Gly  Ala  Lys  Val  Leu  Asn  Leu  Ser  Leu  Gly  Cys  Glu  Cys
                    245                      250                      255

Asn  Ser  Thr  Thr  Leu  Lys  Ser  Ala  Val  Asp  Tyr  Ala  Trp  Asn  Lys  Gly
               260                      265                      270

Ala  Val  Val  Val  Ala  Ala  Ala  Gly  Asn  Asp  Asn  Val  Ser  Arg  Thr  Phe
          275                      280                      285

Gln  Pro  Ala  Ser  Tyr  Pro  Asn  Ala  Ile  Ala  Val  Gly  Ala  Ile  Asp  Ser
     290                      295                      300

Asn  Asp  Arg  Lys  Ala  Ser  Phe  Ser  Asn  Tyr  Gly  Thr  Trp  Val  Asp  Val
305                           310                      315                      320

Thr  Ala  Pro  Gly  Val  Asn  Ile  Ala  Ser  Thr  Val  Pro  Asn  Asn  Gly  Tyr
                    325                      330                      335

Ser  Tyr  Met  Ser  Gly  Thr  Ser  Met  Ala  Ser  Pro  His  Val  Ala  Gly  Leu
               340                      345                      350

Ala  Ala  Leu  Leu  Ala  Ser  Gln  Gly  Lys  Asn  Asn  Val  Gln  Ile  Arg  Gln
          355                      360                      365

Ala  Ile  Glu  Gln  Thr  Ala  Asp  Lys  Ile  Ser  Gly  Thr  Gly  Thr  Asn  Phe
     370                      375                      380

Lys  Tyr  Gly  Lys  Ile  Asn  Ser  Asn  Lys  Ala  Val  Arg  Tyr
385                      390                      395
```

( 2 ) INFORMATION FOR SEQ ID NO:5:

( i ) SEQUENCE CHARACTERISTICS:
    ( A ) LENGTH: 1110 base pairs
    ( B ) TYPE: nucleic acid
    ( C ) STRANDEDNESS: single
    ( D ) TOPOLOGY: linear ( i x ) FEATURE:
    ( A ) NAME/KEY: CDS
    ( B ) LOCATION: 1..1110

( x i ) SEQUENCE DESCRIPTION: SEQ ID NO:5:

```
AAG  GAA  GCA  CCG  AAA  CCG  TTC  CAA  CCT  ATC  AAC  AAA  ACT  TTG  GAT  AAA        48
Lys  Glu  Ala  Pro  Lys  Pro  Phe  Gln  Pro  Ile  Asn  Lys  Thr  Leu  Asp  Lys
          400                      405                      410

GGC  GCT  TTC  GAA  TCC  GGT  GAA  GTC  ATC  GTC  AAA  TTC  AAA  GAT  GGT  GTA        96
Gly  Ala  Phe  Glu  Ser  Gly  Glu  Val  Ile  Val  Lys  Phe  Lys  Asp  Gly  Val
          415                      420                      425

TCC  AAA  AAG  GCA  CAA  GGT  TCT  GCT  CTG  AAC  AAA  GCG  GAG  GCA  AAT  GAA       144
Ser  Lys  Lys  Ala  Gln  Gly  Ser  Ala  Leu  Asn  Lys  Ala  Glu  Ala  Asn  Glu
430                      435                      440                      445

CAG  AAA  GCA  TCA  GCA  AAA  GAT  CCA  TTT  CAG  GTA  TTG  GAA  GTA  GCG  GAC       192
Gln  Lys  Ala  Ser  Ala  Lys  Asp  Pro  Phe  Gln  Val  Leu  Glu  Val  Ala  Asp
               450                      455                      460

GTC  GAT  CAA  GCT  GTT  AAA  GCA  CTG  GAA  AAC  AAT  CCG  AAT  GTA  GAA  TAT       240
Val  Asp  Gln  Ala  Val  Lys  Ala  Leu  Glu  Asn  Asn  Pro  Asn  Val  Glu  Tyr
               465                      470                      475

GCT  GAA  CCA  AAC  TAT  ACC  TTC  CAA  GCG  ACT  TGG  TCA  CCG  AAT  GAC  CCT       288
Ala  Glu  Pro  Asn  Tyr  Thr  Phe  Gln  Ala  Thr  Trp  Ser  Pro  Asn  Asp  Pro
```

| | | | | | | | | | | | | | | | |
|---|---|---|---|---|---|---|---|---|---|---|---|---|---|---|---|
| | | 480 | | | | 485 | | | | | | 490 | | | |
| TAC | TAT | TCT | GCT | TAC | CAG | TAT | GGA | CCA | CAA | AAC | ACC | TCA | ACC | CCT | GCT | 336
| Tyr | Tyr | Ser | Ala | Tyr | Gln | Tyr | Gly | Pro | Gln | Asn | Thr | Ser | Thr | Pro | Ala |
| | 495 | | | | 500 | | | | | 505 | | | | | |
| GCC | TGG | GAT | GTA | ACC | CGT | GGA | AGC | AGC | ACT | CAA | ACG | GTG | GCG | GTC | CTT | 384
| Ala | Trp | Asp | Val | Thr | Arg | Gly | Ser | Ser | Thr | Gln | Thr | Val | Ala | Val | Leu |
| 510 | | | | | 515 | | | | 520 | | | | | | 525 |
| GAT | TCC | GGA | GTG | GAT | TAT | AAC | CAC | CCT | GAT | CTT | GCA | AGA | AAA | GTA | ATA | 432
| Asp | Ser | Gly | Val | Asp | Tyr | Asn | His | Pro | Asp | Leu | Ala | Arg | Lys | Val | Ile |
| | | | | 530 | | | | 535 | | | | | 540 | | |
| AAA | GGG | TAC | GAC | TTT | ATC | GAC | AGG | GAC | AAT | AAC | CCA | ATG | GAT | CTT | AAC | 480
| Lys | Gly | Tyr | Asp | Phe | Ile | Asp | Arg | Asp | Asn | Asn | Pro | Met | Asp | Leu | Asn |
| | | | 545 | | | | 550 | | | | | 555 | | | |
| GGA | CAT | GGT | ACC | CAT | GTT | GCC | GGT | ACT | GTT | GCT | GCT | GAT | ACG | AAC | AAT | 528
| Gly | His | Gly | Thr | His | Val | Ala | Gly | Thr | Val | Ala | Ala | Asp | Thr | Asn | Asn |
| | | 560 | | | | 565 | | | | | 570 | | | | |
| GGA | ATT | GGC | GTA | GCC | GGT | ATG | GCA | CCA | GAT | ACG | AAG | ATC | CTT | GCC | GTA | 576
| Gly | Ile | Gly | Val | Ala | Gly | Met | Ala | Pro | Asp | Thr | Lys | Ile | Leu | Ala | Val |
| | 575 | | | | 580 | | | | | 585 | | | | | |
| CGG | GTC | CTT | GAT | GCC | AAT | GGA | AGT | GGC | TCA | CTT | GAC | AGC | ATT | GCC | TCA | 624
| Arg | Val | Leu | Asp | Ala | Asn | Gly | Ser | Gly | Ser | Leu | Asp | Ser | Ile | Ala | Ser |
| 590 | | | | | 595 | | | | 600 | | | | | | 605 |
| GGT | ATC | CGC | TAT | GCT | GCT | GAT | CAA | GGG | GCA | AAG | GTA | CTC | AAC | CTC | TCC | 672
| Gly | Ile | Arg | Tyr | Ala | Ala | Asp | Gln | Gly | Ala | Lys | Val | Leu | Asn | Leu | Ser |
| | | | 610 | | | | 615 | | | | | 620 | | | |
| CTT | GGT | TGC | GAA | TGC | AAC | TCC | ACA | ACT | CTT | AAG | AGT | GCC | GTC | GAC | TAT | 720
| Leu | Gly | Cys | Glu | Cys | Asn | Ser | Thr | Thr | Leu | Lys | Ser | Ala | Val | Asp | Tyr |
| | | | 625 | | | | 630 | | | | | 635 | | | |
| GCA | TGG | AAC | AAA | GGA | GCT | GTA | GTC | GTT | GCT | GCT | GCA | GGG | AAT | GAC | AAT | 768
| Ala | Trp | Asn | Lys | Gly | Ala | Val | Val | Val | Ala | Ala | Ala | Gly | Asn | Asp | Asn |
| | | 640 | | | | 645 | | | | | 650 | | | | |
| GTA | TCC | CGT | ACA | TTC | CAA | CCA | GCT | TCT | TAC | CCT | AAT | GCC | ATT | GCA | GTA | 816
| Val | Ser | Arg | Thr | Phe | Gln | Pro | Ala | Ser | Tyr | Pro | Asn | Ala | Ile | Ala | Val |
| | 655 | | | | 660 | | | | | 665 | | | | | |
| GGT | GCC | ATT | GAC | TCC | AAT | GAT | CGA | AAA | GCA | TCA | TTC | TCC | AAT | TAC | GGA | 864
| Gly | Ala | Ile | Asp | Ser | Asn | Asp | Arg | Lys | Ala | Ser | Phe | Ser | Asn | Tyr | Gly |
| 670 | | | | | 675 | | | | 680 | | | | | | 685 |
| ACG | TGG | GTG | GAT | GTC | ACT | GCT | CCA | GGT | GTG | AAC | ATA | GCA | TCA | ACC | GTT | 912
| Thr | Trp | Val | Asp | Val | Thr | Ala | Pro | Gly | Val | Asn | Ile | Ala | Ser | Thr | Val |
| | | | 690 | | | | 695 | | | | | 700 | | | |
| CCG | AAT | AAT | GGC | TAC | TCC | TAC | ATG | TCT | GGT | ACG | TCC | ATG | GCA | TCC | CCT | 960
| Pro | Asn | Asn | Gly | Tyr | Ser | Tyr | Met | Ser | Gly | Thr | Ser | Met | Ala | Ser | Pro |
| | | | 705 | | | | 710 | | | | | 715 | | | |
| CAC | GTG | GCC | GGT | TTG | GCT | GCT | TTG | TTG | GCA | AGT | CAA | GGT | AAG | AAT | AAC | 1008
| His | Val | Ala | Gly | Leu | Ala | Ala | Leu | Leu | Ala | Ser | Gln | Gly | Lys | Asn | Asn |
| | | 720 | | | | 725 | | | | | 730 | | | | |
| GTA | CAA | ATC | CGC | CAG | GCC | ATT | GAG | CAA | ACC | GCC | GAT | AAG | ATC | TCT | GGC | 1056
| Val | Gln | Ile | Arg | Gln | Ala | Ile | Glu | Gln | Thr | Ala | Asp | Lys | Ile | Ser | Gly |
| | 735 | | | | 740 | | | | | 745 | | | | | |
| ACT | GGA | ACA | AAC | TTC | AAG | TAT | GGT | AAA | ATC | AAC | TCA | AAC | AAA | GCT | GTA | 1104
| Thr | Gly | Thr | Asn | Phe | Lys | Tyr | Gly | Lys | Ile | Asn | Ser | Asn | Lys | Ala | Val |
| 750 | | | | | 755 | | | | 760 | | | | | | 765 |
| AGA | TAC | | | | | | | | | | | | | | | 1110
| Arg | Tyr | | | | | | | | | | | | | | |

( 2 ) INFORMATION FOR SEQ ID NO:6:

( i ) SEQUENCE CHARACTERISTICS:
( A ) LENGTH: 370 amino acids
( B ) TYPE: amino acid
( D ) TOPOLOGY: linear ( i i ) MOLECULE TYPE: protein ( x i ) SEQUENCE DESCRIPTION: SEQ ID NO:6:

```
Lys Glu Ala Pro Lys Pro Phe Gln Pro Ile Asn Lys Thr Leu Asp Lys
 1               5                  10                  15

Gly Ala Phe Glu Ser Gly Glu Val Ile Val Lys Phe Lys Asp Gly Val
                20                  25                  30

Ser Lys Lys Ala Gln Gly Ser Ala Leu Asn Lys Ala Glu Ala Asn Glu
            35                  40                  45

Gln Lys Ala Ser Ala Lys Asp Pro Phe Gln Val Leu Glu Val Ala Asp
    50                  55                  60

Val Asp Gln Ala Val Lys Ala Leu Glu Asn Asn Pro Asn Val Glu Tyr
65                  70                  75                  80

Ala Glu Pro Asn Tyr Thr Phe Gln Ala Thr Trp Ser Pro Asn Asp Pro
                85                  90                  95

Tyr Tyr Ser Ala Tyr Gln Tyr Gly Pro Gln Asn Thr Ser Thr Pro Ala
                100                 105                 110

Ala Trp Asp Val Thr Arg Gly Ser Ser Thr Gln Thr Val Ala Val Leu
            115                 120                 125

Asp Ser Gly Val Asp Tyr Asn His Pro Asp Leu Ala Arg Lys Val Ile
    130                 135                 140

Lys Gly Tyr Asp Phe Ile Asp Arg Asp Asn Asn Pro Met Asp Leu Asn
145                 150                 155                 160

Gly His Gly Thr His Val Ala Gly Thr Val Ala Ala Asp Thr Asn Asn
                165                 170                 175

Gly Ile Gly Val Ala Gly Met Ala Pro Asp Thr Lys Ile Leu Ala Val
                180                 185                 190

Arg Val Leu Asp Ala Asn Gly Ser Gly Ser Leu Asp Ser Ile Ala Ser
            195                 200                 205

Gly Ile Arg Tyr Ala Ala Asp Gln Gly Ala Lys Val Leu Asn Leu Ser
    210                 215                 220

Leu Gly Cys Glu Cys Asn Ser Thr Thr Leu Lys Ser Ala Val Asp Tyr
225                 230                 235                 240

Ala Trp Asn Lys Gly Ala Val Val Val Ala Ala Gly Asn Asp Asn
                245                 250                 255

Val Ser Arg Thr Phe Gln Pro Ala Ser Tyr Pro Asn Ala Ile Ala Val
            260                 265                 270

Gly Ala Ile Asp Ser Asn Asp Arg Lys Ala Ser Phe Ser Asn Tyr Gly
    275                 280                 285

Thr Trp Val Asp Val Thr Ala Pro Gly Val Asn Ile Ala Ser Thr Val
290                 295                 300

Pro Asn Asn Gly Tyr Ser Tyr Met Ser Gly Thr Ser Met Ala Ser Pro
305                 310                 315                 320

His Val Ala Gly Leu Ala Ala Leu Leu Ala Ser Gln Gly Lys Asn Asn
                325                 330                 335

Val Gln Ile Arg Gln Ala Ile Glu Gln Thr Ala Asp Lys Ile Ser Gly
            340                 345                 350

Thr Gly Thr Asn Phe Lys Tyr Gly Lys Ile Asn Ser Asn Lys Ala Val
        355                 360                 365

Arg Tyr
    370
```

( 2 ) INFORMATION FOR SEQ ID NO:7:

-continued (i) SEQUENCE CHARACTERISTICS:
  (A) LENGTH: 840 base pairs
  (B) TYPE: nucleic acid
  (C) STRANDEDNESS: single
  (D) TOPOLOGY: linear (ix) FEATURE:
  (A) NAME/KEY: CDS
  (B) LOCATION: 1..840

(xi) SEQUENCE DESCRIPTION: SEQ ID NO:7:

| TGG | TCA | CCG | AAT | GAC | CCT | TAC | TAT | TCT | GCT | TAC | CAG | TAT | GGA | CCA | CAA | 48 |
| Trp | Ser | Pro | Asn | Asp | Pro | Tyr | Tyr | Ser | Ala | Tyr | Gln | Tyr | Gly | Pro | Gln | |
| | | | 375 | | | | | 380 | | | | | 385 | | | |

| AAC | ACC | TCA | ACC | CCT | GCT | GCC | TGG | GAT | GTA | ACC | CGT | GGA | AGC | AGC | ACT | 96 |
| Asn | Thr | Ser | Thr | Pro | Ala | Ala | Trp | Asp | Val | Thr | Arg | Gly | Ser | Ser | Thr | |
| | | | 390 | | | | | 395 | | | | | 400 | | | |

| CAA | ACG | GTG | GCG | GTC | CTT | GAT | TCC | GGA | GTG | GAT | TAT | AAC | CAC | CCT | GAT | 144 |
| Gln | Thr | Val | Ala | Val | Leu | Asp | Ser | Gly | Val | Asp | Tyr | Asn | His | Pro | Asp | |
| | | 405 | | | | | 410 | | | | | 415 | | | | |

| CTT | GCA | AGA | AAA | GTA | ATA | AAA | GGG | TAC | GAC | TTT | ATC | GAC | AGG | GAC | AAT | 192 |
| Leu | Ala | Arg | Lys | Val | Ile | Lys | Gly | Tyr | Asp | Phe | Ile | Asp | Arg | Asp | Asn | |
| | 420 | | | | 425 | | | | | 430 | | | | | | |

| AAC | CCA | ATG | GAT | CTT | AAC | GGA | CAT | GGT | ACC | CAT | GTT | GCC | GGT | ACT | GTT | 240 |
| Asn | Pro | Met | Asp | Leu | Asn | Gly | His | Gly | Thr | His | Val | Ala | Gly | Thr | Val | |
| 435 | | | | 440 | | | | | 445 | | | | | 450 | | |

| GCT | GCT | GAT | ACG | AAC | AAT | GGA | ATT | GGC | GTA | GCC | GGT | ATG | GCA | CCA | GAT | 288 |
| Ala | Ala | Asp | Thr | Asn | Asn | Gly | Ile | Gly | Val | Ala | Gly | Met | Ala | Pro | Asp | |
| | | | | 455 | | | | | 460 | | | | | 465 | | |

| ACG | AAG | ATC | CTT | GCC | GTA | CGG | GTC | CTT | GAT | GCC | AAT | GGA | AGT | GGC | TCA | 336 |
| Thr | Lys | Ile | Leu | Ala | Val | Arg | Val | Leu | Asp | Ala | Asn | Gly | Ser | Gly | Ser | |
| | | | 470 | | | | | 475 | | | | | 480 | | | |

| CTT | GAC | AGC | ATT | GCC | TCA | GGT | ATC | CGC | TAT | GCT | GCT | GAT | CAA | GGG | GCA | 384 |
| Leu | Asp | Ser | Ile | Ala | Ser | Gly | Ile | Arg | Tyr | Ala | Ala | Asp | Gln | Gly | Ala | |
| | | 485 | | | | | 490 | | | | | 495 | | | | |

| AAG | GTA | CTC | AAC | CTC | TCC | CTT | GGT | TGC | GAA | TGC | AAC | TCC | ACA | ACT | CTT | 432 |
| Lys | Val | Leu | Asn | Leu | Ser | Leu | Gly | Cys | Glu | Cys | Asn | Ser | Thr | Thr | Leu | |
| | 500 | | | | 505 | | | | | 510 | | | | | | |

| AAG | AGT | GCC | GTC | GAC | TAT | GCA | TGG | AAC | AAA | GGA | GCT | GTA | GTC | GTT | GCT | 480 |
| Lys | Ser | Ala | Val | Asp | Tyr | Ala | Trp | Asn | Lys | Gly | Ala | Val | Val | Val | Ala | |
| 515 | | | | 520 | | | | | 525 | | | | | 530 | | |

| GCT | GCA | GGG | AAT | GAC | AAT | GTA | TCC | CGT | ACA | TTC | CAA | CCA | GCT | TCT | TAC | 528 |
| Ala | Ala | Gly | Asn | Asp | Asn | Val | Ser | Arg | Thr | Phe | Gln | Pro | Ala | Ser | Tyr | |
| | | | | 535 | | | | | 540 | | | | | 545 | | |

| CCT | AAT | GCC | ATT | GCA | GTA | GGT | GCC | ATT | GAC | TCC | AAT | GAT | CGA | AAA | GCA | 576 |
| Pro | Asn | Ala | Ile | Ala | Val | Gly | Ala | Ile | Asp | Ser | Asn | Asp | Arg | Lys | Ala | |
| | | | 550 | | | | | 555 | | | | | 560 | | | |

| TCA | TTC | TCC | AAT | TAC | GGA | ACG | TGG | GTG | GAT | GTC | ACT | GCT | CCA | GGT | GTG | 624 |
| Ser | Phe | Ser | Asn | Tyr | Gly | Thr | Trp | Val | Asp | Val | Thr | Ala | Pro | Gly | Val | |
| | | 565 | | | | | 570 | | | | | 575 | | | | |

| AAC | ATA | GCA | TCA | ACC | GTT | CCG | AAT | AAT | GGC | TAC | TCC | TAC | ATG | TCT | GGT | 672 |
| Asn | Ile | Ala | Ser | Thr | Val | Pro | Asn | Asn | Gly | Tyr | Ser | Tyr | Met | Ser | Gly | |
| | 580 | | | | 585 | | | | | 590 | | | | | | |

| ACG | TCC | ATG | GCA | TCC | CCT | CAC | GTG | GCC | GGT | TTG | GCT | GCT | TTG | TTG | GCA | 720 |
| Thr | Ser | Met | Ala | Ser | Pro | His | Val | Ala | Gly | Leu | Ala | Ala | Leu | Leu | Ala | |
| 595 | | | | 600 | | | | | 605 | | | | | 610 | | |

| AGT | CAA | GGT | AAG | AAT | AAC | GTA | CAA | ATC | CGC | CAG | GCC | ATT | GAG | CAA | ACC | 768 |
| Ser | Gln | Gly | Lys | Asn | Asn | Val | Gln | Ile | Arg | Gln | Ala | Ile | Glu | Gln | Thr | |
| | | | | 615 | | | | | 620 | | | | | 625 | | |

| GCC | GAT | AAG | ATC | TCT | GGC | ACT | GGA | ACA | AAC | TTC | AAG | TAT | GGT | AAA | ATC | 816 |
| Ala | Asp | Lys | Ile | Ser | Gly | Thr | Gly | Thr | Asn | Phe | Lys | Tyr | Gly | Lys | Ile | |
| | | | 630 | | | | | 635 | | | | | 640 | | | |

```
AAC  TCA  AAC  AAA  GCT  GTA  AGA  TAC                                               840
Asn  Ser  Asn  Lys  Ala  Val  Arg  Tyr
          645                      650
```

(2) INFORMATION FOR SEQ ID NO:8:

(i) SEQUENCE CHARACTERISTICS:
　　　　(A) LENGTH: 280 amino acids
　　　　(B) TYPE: amino acid
　　　　(D) TOPOLOGY: linear (ii) MOLECULE TYPE: protein (xi) SEQUENCE DESCRIPTION: SEQ ID NO:8:

```
Trp  Ser  Pro  Asn  Asp  Pro  Tyr  Tyr  Ser  Ala  Tyr  Gln  Tyr  Gly  Pro  Gln
 1              5                       10                       15

Asn  Thr  Ser  Thr  Pro  Ala  Ala  Trp  Asp  Val  Thr  Arg  Gly  Ser  Ser  Thr
          20                       25                       30

Gln  Thr  Val  Ala  Val  Leu  Asp  Ser  Gly  Val  Asp  Tyr  Asn  His  Pro  Asp
          35                       40                       45

Leu  Ala  Arg  Lys  Val  Ile  Lys  Gly  Tyr  Asp  Phe  Ile  Asp  Arg  Asp  Asn
     50                       55                       60

Asn  Pro  Met  Asp  Leu  Asn  Gly  His  Gly  Thr  His  Val  Ala  Gly  Thr  Val
65                       70                       75                       80

Ala  Ala  Asp  Thr  Asn  Asn  Gly  Ile  Gly  Val  Ala  Gly  Met  Ala  Pro  Asp
                    85                       90                       95

Thr  Lys  Ile  Leu  Ala  Val  Arg  Val  Leu  Asp  Ala  Asn  Gly  Ser  Gly  Ser
               100                      105                      110

Leu  Asp  Ser  Ile  Ala  Ser  Gly  Ile  Arg  Tyr  Ala  Ala  Asp  Gln  Gly  Ala
          115                      120                      125

Lys  Val  Leu  Asn  Leu  Ser  Leu  Gly  Cys  Glu  Cys  Asn  Ser  Thr  Thr  Leu
130                      135                      140

Lys  Ser  Ala  Val  Asp  Tyr  Ala  Trp  Asn  Lys  Gly  Ala  Val  Val  Val  Ala
145                      150                      155                      160

Ala  Ala  Gly  Asn  Asp  Asn  Val  Ser  Arg  Thr  Phe  Gln  Pro  Ala  Ser  Tyr
                    165                      170                      175

Pro  Asn  Ala  Ile  Ala  Val  Gly  Ala  Ile  Asp  Ser  Asn  Asp  Arg  Lys  Ala
               180                      185                      190

Ser  Phe  Ser  Asn  Tyr  Gly  Thr  Trp  Val  Asp  Val  Thr  Ala  Pro  Gly  Val
          195                      200                      205

Asn  Ile  Ala  Ser  Thr  Val  Pro  Asn  Asn  Gly  Tyr  Ser  Tyr  Met  Ser  Gly
     210                      215                      220

Thr  Ser  Met  Ala  Ser  Pro  His  Val  Ala  Gly  Leu  Ala  Ala  Leu  Leu  Ala
225                      230                      235                      240

Ser  Gln  Gly  Lys  Asn  Asn  Val  Gln  Ile  Arg  Gln  Ala  Ile  Glu  Gln  Thr
                    245                      250                      255

Ala  Asp  Lys  Ile  Ser  Gly  Thr  Gly  Thr  Asn  Phe  Lys  Tyr  Gly  Lys  Ile
               260                      265                      270

Asn  Ser  Asn  Lys  Ala  Val  Arg  Tyr
          275                      280
```

(2) INFORMATION FOR SEQ ID NO:9:

(i) SEQUENCE CHARACTERISTICS:
　　　　(A) LENGTH: 679 base pairs
　　　　(B) TYPE: nucleic acid
　　　　(C) STRANDEDNESS: single
　　　　(D) TOPOLOGY: linear (xi) SEQUENCE DESCRIPTION: SEQ ID NO:9:

```
AAGCTTAATC  ATCCCGATGT  ATCGCTTCAG  CGCTTACCGT  AGACGATTTT  CTTTATAGTC    60

TCGATGGATA  AAAAGTACCT  ATCTGAAATG  GAAGCAATCG  ACTCTCCTCC  AGTAAAGGCT   120

TCAAGGATCG  ACGTGTTTCT  CCGTTTAAGC  GCTTCCCTTC  CTCCTGACTT  TGAGCCCCAG   180

GCATTATACT  CTTCTTTTCG  CTTTGGGATA  TAAATGGTTT  GGCCTTGAAC  ATAGTTTTGT   240

AATTCTCTCA  TTAAGTAATC  AGGAATTTGA  TTTACTGCTT  TCAATCGTGT  CAGCTCCTTA   300

TCATTATTGG  ATCAATAAGG  GACAAAGCCG  ACATATGAAT  GGCGATTCAT  CTAAAACTAC   360

CACCCCATGC  AAAGGATCGC  CGAATCATAC  AGGCTTTGCA  TGAGATGCTG  CAGATTTCGG   420

AAAACGGATT  TCCATATGAT  CACCTCCTAG  TATCAGTATA  CTGATACTAG  CAGAAAGATT   480

TCCATAAGAA  TTTCTTATAG  TTACCATAAT  ATTATTATAT  AAACCTACTA  TATTTGATTT   540

TCAATTTGAG  AAAATAAGTG  ACCATTCACC  TATCCTTAAA  GTTGCTCAAC  CCCATACAAT   600

CATGAAACTT  TTCATGCCAA  ACGTTCATTA  TGCGAAATCT  ATCAAAAACT  GAGAGTGAAT   660

TCATTTTTTG  ATAGAAAAT                                                    679
```

( 2 ) INFORMATION FOR SEQ ID NO:10:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..81

( x i ) SEQUENCE DESCRIPTION: SEQ ID NO:10:

```
ATG  AAG  TTC  AAA  AAA  ATA  GCC  GCT  CTA  TCC  TTA  GCA  ACT  TCC  CTT  GCT    48
Met  Lys  Phe  Lys  Lys  Ile  Ala  Ala  Leu  Ser  Leu  Ala  Thr  Ser  Leu  Ala
                    285                     290                     295

TTA  TTC  CCT  GCC  TTC  GGA  GGT  AGT  TCA  CTG  GCC                              81
Leu  Phe  Pro  Ala  Phe  Gly  Gly  Ser  Ser  Leu  Ala
                    300                     305
```

( 2 ) INFORMATION FOR SEQ ID NO:11:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Met  Lys  Phe  Lys  Lys  Ile  Ala  Ala  Leu  Ser  Leu  Ala  Thr  Ser  Leu  Ala
 1                    5                      10                      15

Leu  Phe  Pro  Ala  Phe  Gly  Gly  Ser  Ser  Leu  Ala
                    20                      25
```

( 2 ) INFORMATION FOR SEQ ID NO:12:

( i ) SEQUENCE CHARACTERISTICS:
        ( A ) LENGTH: 873 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..873

( x i ) SEQUENCE DESCRIPTION: SEQ ID NO:12:

| | | | | | | | | | | | | | | | | |
|---|---|---|---|---|---|---|---|---|---|---|---|---|---|---|---|---|
| ATG | AGG | AGC | TCC | CTT | GTG | CTG | TTC | TTT | GTC | TCT | GCG | TGG | ACG | GCC | TTG | 48 |
| Met | Arg | Ser | Ser | Leu | Val | Leu | Phe | Phe | Val | Ser | Ala | Trp | Thr | Ala | Leu | |
| | | 30 | | | | | 35 | | | | | 40 | | | | |
| GCC | AGT | CCT | ATT | CGT | CGA | GAG | GTC | TCG | CAG | GAT | CTG | TTT | AAC | CAG | TTC | 96 |
| Ala | Ser | Pro | Ile | Arg | Arg | Glu | Val | Ser | Gln | Asp | Leu | Phe | Asn | Gln | Phe | |
| | 45 | | | | | 50 | | | | | 55 | | | | | |
| AAT | CTC | TTT | GCA | CAG | TAT | TCT | GCA | GCC | GCA | TAC | TGC | GGA | AAA | AAC | AAT | 144 |
| Asn | Leu | Phe | Ala | Gln | Tyr | Ser | Ala | Ala | Ala | Tyr | Cys | Gly | Lys | Asn | Asn | |
| 60 | | | | | 65 | | | | | 70 | | | | | 75 | |
| GAT | GCC | CCA | GCT | GGT | ACA | AAC | ATT | ACG | TGC | ACG | GGA | AAT | GCC | TGC | CCC | 192 |
| Asp | Ala | Pro | Ala | Gly | Thr | Asn | Ile | Thr | Cys | Thr | Gly | Asn | Ala | Cys | Pro | |
| | | | | 80 | | | | | 85 | | | | | 90 | | |
| GAG | GTA | GAG | AAG | GCG | GAT | GCA | ACG | TTT | CTC | TAC | TCG | TTT | GAA | GAC | TCT | 240 |
| Glu | Val | Glu | Lys | Ala | Asp | Ala | Thr | Phe | Leu | Tyr | Ser | Phe | Glu | Asp | Ser | |
| | | | 95 | | | | | 100 | | | | | 105 | | | |
| GGA | GTG | GGC | GAT | GTC | ACC | GGC | TTC | CTT | GCT | CTC | GAC | AAC | ACG | AAC | AAA | 288 |
| Gly | Val | Gly | Asp | Val | Thr | Gly | Phe | Leu | Ala | Leu | Asp | Asn | Thr | Asn | Lys | |
| | | | 110 | | | | | 115 | | | | | 120 | | | |
| TTG | ATC | GTC | CTC | TCT | TTC | CGT | GGC | TCT | CGT | TCC | ATA | GAG | AAC | TGG | ATC | 336 |
| Leu | Ile | Val | Leu | Ser | Phe | Arg | Gly | Ser | Arg | Ser | Ile | Glu | Asn | Trp | Ile | |
| | 125 | | | | | 130 | | | | | 135 | | | | | |
| GGG | AAT | CTT | AAC | TTC | GAC | TTG | AAA | GAA | ATA | AAT | GAC | ATT | TGC | TCC | GGC | 384 |
| Gly | Asn | Leu | Asn | Phe | Asp | Leu | Lys | Glu | Ile | Asn | Asp | Ile | Cys | Ser | Gly | |
| 140 | | | | | 145 | | | | | 150 | | | | | 155 | |
| TGC | AGG | GGA | CAT | GAC | GGC | TTC | ACT | TCG | TCC | TGG | AGG | TCT | GTA | GCC | GAT | 432 |
| Cys | Arg | Gly | His | Asp | Gly | Phe | Thr | Ser | Ser | Trp | Arg | Ser | Val | Ala | Asp | |
| | | | | 160 | | | | | 165 | | | | | 170 | | |
| ACG | TTA | AGG | CAG | AAG | GTG | GAG | GAT | GCT | GTG | AGG | GAG | CAT | CCC | GAC | TAT | 480 |
| Thr | Leu | Arg | Gln | Lys | Val | Glu | Asp | Ala | Val | Arg | Glu | His | Pro | Asp | Tyr | |
| | | | 175 | | | | | 180 | | | | | 185 | | | |
| CGC | GTG | GTG | TTT | ACC | GGA | CAT | AGC | TTG | GGT | GGT | GCA | TTG | GCA | ACT | GTT | 528 |
| Arg | Val | Val | Phe | Thr | Gly | His | Ser | Leu | Gly | Gly | Ala | Leu | Ala | Thr | Val | |
| | | 190 | | | | | 195 | | | | | 200 | | | | |
| GCC | GGA | GCA | GAC | CTG | CGT | GGA | AAT | GGG | TAT | GAT | ATC | GAC | GTG | TTT | TCA | 576 |
| Ala | Gly | Ala | Asp | Leu | Arg | Gly | Asn | Gly | Tyr | Asp | Ile | Asp | Val | Phe | Ser | |
| | 205 | | | | | 210 | | | | | 215 | | | | | |
| TAT | GGC | GCC | CCC | CGA | GTC | GGA | AAC | AGG | GCT | TTT | GCA | GAA | TTC | CTG | ACC | 624 |
| Tyr | Gly | Ala | Pro | Arg | Val | Gly | Asn | Arg | Ala | Phe | Ala | Glu | Phe | Leu | Thr | |
| 220 | | | | | 225 | | | | | 230 | | | | | 235 | |
| GTA | CAG | ACC | GGC | GGA | ACA | CTC | TAC | CGC | ATT | ACC | CAC | ACC | AAT | GAT | ATT | 672 |
| Val | Gln | Thr | Gly | Gly | Thr | Leu | Tyr | Arg | Ile | Thr | His | Thr | Asn | Asp | Ile | |
| | | | | 240 | | | | | 245 | | | | | 250 | | |
| GTC | CCT | AGA | CTC | CCG | CCG | CGC | GAA | TTC | GGT | TAC | AGC | CAT | TCT | AGC | CCA | 720 |
| Val | Pro | Arg | Leu | Pro | Pro | Arg | Glu | Phe | Gly | Tyr | Ser | His | Ser | Ser | Pro | |
| | | | 255 | | | | | 260 | | | | | 265 | | | |
| GAG | TAC | TGG | ATC | AAA | TCT | GGA | ACC | CTT | GTC | CCC | GTC | ACC | CGA | AAC | GAT | 768 |
| Glu | Tyr | Trp | Ile | Lys | Ser | Gly | Thr | Leu | Val | Pro | Val | Thr | Arg | Asn | Asp | |
| | | 270 | | | | | 275 | | | | | 280 | | | | |
| ATC | GTG | AAG | ATA | GAA | GGC | ATC | GAT | GCC | ACC | GGC | GGC | AAT | AAC | CAG | CCT | 816 |
| Ile | Val | Lys | Ile | Glu | Gly | Ile | Asp | Ala | Thr | Gly | Gly | Asn | Asn | Gln | Pro | |
| | 285 | | | | | 290 | | | | | 295 | | | | | |
| AAC | ATT | CCG | GAT | ATC | CCT | GCG | CAC | CTA | TGG | TAC | TTC | GGG | TTA | ATT | GGG | 864 |
| Asn | Ile | Pro | Asp | Ile | Pro | Ala | His | Leu | Trp | Tyr | Phe | Gly | Leu | Ile | Gly | |
| 300 | | | | | 305 | | | | | 310 | | | | | 315 | |
| ACA | TGT | CTT | | | | | | | | | | | | | | 873 |
| Thr | Cys | Leu | | | | | | | | | | | | | | |

( 2 ) INFORMATION FOR SEQ ID NO:13:

( i ) SEQUENCE CHARACTERISTICS:

( A ) LENGTH: 291 amino acids
( B ) TYPE: amino acid
( D ) TOPOLOGY: linear ( i i ) MOLECULE TYPE: protein ( x i ) SEQUENCE DESCRIPTION: SEQ ID NO:13:

| Met | Arg | Ser | Ser | Leu | Val | Leu | Phe | Phe | Val | Ser | Ala | Trp | Thr | Ala | Leu |
|---|---|---|---|---|---|---|---|---|---|---|---|---|---|---|---|
| 1 | | | | 5 | | | | | 10 | | | | | 15 | |
| Ala | Ser | Pro | Ile | Arg | Arg | Glu | Val | Ser | Gln | Asp | Leu | Phe | Asn | Gln | Phe |
| | | | 20 | | | | 25 | | | | | 30 | | | |
| Asn | Leu | Phe | Ala | Gln | Tyr | Ser | Ala | Ala | Ala | Tyr | Cys | Gly | Lys | Asn | Asn |
| | | 35 | | | | | 40 | | | | | | 45 | | |
| Asp | Ala | Pro | Ala | Gly | Thr | Asn | Ile | Thr | Cys | Thr | Gly | Asn | Ala | Cys | Pro |
| | 50 | | | | | 55 | | | | | | 60 | | | |
| Glu | Val | Glu | Lys | Ala | Asp | Ala | Thr | Phe | Leu | Tyr | Ser | Phe | Glu | Asp | Ser |
| 65 | | | | | 70 | | | | 75 | | | | | | 80 |
| Gly | Val | Gly | Asp | Val | Thr | Gly | Phe | Leu | Ala | Leu | Asp | Asn | Thr | Asn | Lys |
| | | | | 85 | | | | | 90 | | | | | 95 | |
| Leu | Ile | Val | Leu | Ser | Phe | Arg | Gly | Ser | Arg | Ser | Ile | Glu | Asn | Trp | Ile |
| | | | 100 | | | | | 105 | | | | | 110 | | |
| Gly | Asn | Leu | Asn | Phe | Asp | Leu | Lys | Glu | Ile | Asn | Asp | Ile | Cys | Ser | Gly |
| | | | 115 | | | | | 120 | | | | | 125 | | |
| Cys | Arg | Gly | His | Asp | Gly | Phe | Thr | Ser | Ser | Trp | Arg | Ser | Val | Ala | Asp |
| | 130 | | | | | 135 | | | | | 140 | | | | |
| Thr | Leu | Arg | Gln | Lys | Val | Glu | Asp | Ala | Val | Arg | Glu | His | Pro | Asp | Tyr |
| 145 | | | | | 150 | | | | | 155 | | | | | 160 |
| Arg | Val | Val | Phe | Thr | Gly | His | Ser | Leu | Gly | Gly | Ala | Leu | Ala | Thr | Val |
| | | | | 165 | | | | | 170 | | | | | 175 | |
| Ala | Gly | Ala | Asp | Leu | Arg | Gly | Asn | Gly | Tyr | Asp | Ile | Asp | Val | Phe | Ser |
| | | | 180 | | | | | 185 | | | | | 190 | | |
| Tyr | Gly | Ala | Pro | Arg | Val | Gly | Asn | Arg | Ala | Phe | Ala | Glu | Phe | Leu | Thr |
| | | | 195 | | | | | 200 | | | | | 205 | | |
| Val | Gln | Thr | Gly | Gly | Thr | Leu | Tyr | Arg | Ile | Thr | His | Thr | Asn | Asp | Ile |
| | 210 | | | | | 215 | | | | | 220 | | | | |
| Val | Pro | Arg | Leu | Pro | Pro | Arg | Glu | Phe | Gly | Tyr | Ser | His | Ser | Ser | Pro |
| 225 | | | | | 230 | | | | | 235 | | | | | 240 |
| Glu | Tyr | Trp | Ile | Lys | Ser | Gly | Thr | Leu | Val | Pro | Val | Thr | Arg | Asn | Asp |
| | | | | 245 | | | | | 250 | | | | | 255 | |
| Ile | Val | Lys | Ile | Glu | Gly | Ile | Asp | Ala | Thr | Gly | Gly | Asn | Asn | Gln | Pro |
| | | | 260 | | | | | 265 | | | | | 270 | | |
| Asn | Ile | Pro | Asp | Ile | Pro | Ala | His | Leu | Trp | Tyr | Phe | Gly | Leu | Ile | Gly |
| | | 275 | | | | | 280 | | | | | 285 | | | |
| Thr | Cys | Leu | | | | | | | | | | | | | |
| | 290 | | | | | | | | | | | | | | |

( 2 ) INFORMATION FOR SEQ ID NO:14:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( x i ) SEQUENCE DESCRIPTION: SEQ ID NO:14:

| Ala | Tyr | Gln | Tyr | Gly | Pro | Gln | Asn | Thr |
|---|---|---|---|---|---|---|---|---|
| 1 | | | | 5 | | | | |

( 2 ) INFORMATION FOR SEQ ID NO:15:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO:15:

```
Tyr  Asp  Phe  Ile  Asp  Tyr  Asp  Asn  Asn  Pro  Met  Asp
 1              5                        10
```

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GCTACATAGG CCCAAAAC        18

( 2 ) INFORMATION FOR SEQ ID NO:17:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

TCCATGGTTT TTCTATCATA ATCTA        25

( 2 ) INFORMATION FOR SEQ ID NO:18:

( i ) SEQUENCE CHARACTERISTICS:
        ( A ) LENGTH: 628 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

| | | | | | | |
|---|---|---|---|---|---|---|
| GAATTCGGCT | TAAGGCATGC | GTCCTTCTTT | GTGCTTGGAA | GCAGAGCCCA | ATATTATCCC | 60 |
| GAAACGATAA | AACGGATGCT | GAAGGAAGGA | AACGAAGTCG | GCAACCATTC | CTGGGACCAT | 120 |
| CCGTTATTGA | CAAGGCTGTC | AAACGAAAAA | GCGTATCAGG | AGATTAACGA | CACGCAAGAA | 180 |
| ATGATCGAAA | AAATCAGCGG | ACACCTGCCT | GTACACTTGC | GTCCTCCATA | CGGCGGGATC | 240 |
| AATGATTCCG | TCCGCTCGCT | TTCCAATCTG | AAGGTTTCAT | TGTGGGATGT | TGATCCGGAA | 300 |
| GATTGGAAGT | ACAAAAATAA | GCAAAAGATT | GTCAATCATG | TCATGAGCCA | TGCGGGAGAC | 360 |
| GGAAAAATCG | TCTTAATGCA | CGATATTTAT | GCAACGTTCG | CAGATGCTGC | TGAAGAGATT | 420 |
| ATTAAAAAGC | TGAAAGCAAA | AGGCTATCAA | TTGGTAACTG | TATCTCAGCT | TGAAGAAGTG | 480 |
| AAGAAGCAGA | GAGGCTATTG | AATAAATGAG | TAGAAAGCGC | CATATCGGCG | CTTTTCTTTT | 540 |
| GGAAGAAAAT | ATAGGGAAAA | TGGTACTTGT | TAAAAATTCG | GAATATTTAT | ACAATATCAT | 600 |
| ATGTTACACA | TTGAAAGAAG | CCGAATTC | | | | 628 |

( 2 ) INFORMATION FOR SEQ ID NO:19:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

AAGGCATGCG TCCTTC                                                                          16

( 2 ) INFORMATION FOR SEQ ID NO:20:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

CTTTCAATGT GTAACATA                                                                        18

( 2 ) INFORMATION FOR SEQ ID NO:21:

( i ) SEQUENCE CHARACTERISTICS:
        ( A ) LENGTH: 1514 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

```
GAATTCGGCT  TGAGACCCGG  GAGCTTTCAG  TGAAGTACGT  GATTATACGG  AGATGAAAAT     60
TCGTACACTG  TTAACGAGAA  GGAAACGCCG  ACGAAAGCGT  AGCATCGGAT  GGCAAAGATG    120
GAGTAACGAA  TATCTCTACG  GTGTACTGGG  GCTTTACTGA  GACTAGAAAG  TCCTTCCCTT    180
GAAAAGTGCA  GAGAGTTTTC  GATAAAGTG   TCAGCCATTT  GATAAGTCTC  ATTCTCATAA    240
CCTATTGATG  AAGTTTATAG  GGAAGCTGCT  TGAGAGGGAA  AACCTCACGA  ACAGTTCTTA    300
TGGGGAGAGA  CTGGAAACAG  GTCACAATTG  ATACCTCGCT  AATCTTTTAA  CCGACAAAGT    360
TTTTTTAAAC  CGTGGAAGTC  ATAATAACCT  GGATATTGTG  AATTTATAAA  AGTTAACAAA    420
TGGTTATAT   TAAGACAGTC  ATAAACCAAA  GATTTTTCTT  CTAAAGCTAC  GATAGCAAAA    480
ATTTCACTAG  AAATTAGTTA  TACAAGCATT  TTGTAAGAAT  TATTAAAAAG  ATAAATCCTG    540
CTATTACGAG  ATTAGTAGGA  TGATATTGTG  AAAAATTTTT  TATCTATTCG  ATTTAAAATA    600
TTTATGAATT  TTACATAAAC  CTCATAAGAA  AAAATACTAT  CTATACTATT  TTAAGAAATT    660
TATTAGAATA  AGCGGATTCA  AAATAGCCCT  GGCCATAAAA  GTACCTCAGC  AGTAGAAGTT    720
TTGACCAAAA  TTAAAAAAAT  ACCCAATCAA  GAGAATATTC  TTAATTACAA  TACGTTTTGC    780
GAGGAACATA  TTGATTGAAA  TTTAATAAAT  TTAGTCCTAA  AATTTAAAGA  AATTTAAGTT    840
TTTCATATTT  TTATGAACTA  ACAAGAATAA  AAATTGTGTT  TATTTATTAT  TCTTGTTAAA    900
TATTTGATAA  AGAGATATAT  TTTTGGTCGA  AACGTAAGAT  GAAACCTTAG  ATAAAAGTGC    960
TTTTTTTGTT  GCAATTGAAG  AATTATTAAT  GTTAAGCTTA  ATTAAAGATA  ATATCTTTGA   1020
ATTGTAACGC  CCCTCAAAAG  TAAGAACTAC  AAAAAAAGAA  TACGTTATAT  AGAAATATGT   1080
TTGAACCTTC  TTCAGATTAC  AAATATATTC  GGACGGACTC  TACCTCAAAT  GCTTATCTAA   1140
CTATAGAATG  ACATACAAGC  ACAACCTTGA  AAATTTGAAA  ATATAACTAC  CAATGAACTT   1200
GTTCATGTGA  ATTATCGCTG  TATTTAATTT  TCTCAATTCA  ATATATAATA  TGCCAATACA   1260
TTGTTACAAG  TAGAAATTAA  GACACCCTTG  ATAGCCTTAC  TATACCTAAC  ATGATGTAGT   1320
ATTAAATGAA  TATGTAAATA  TATTTATGAT  AAGAAGCGAC  TTATTTATAA  TCATTACATA   1380
TTTTTCTATT  GGAATGATTA  AGATTCCAAT  AGAATAGTGT  ATAAATTATT  TATCTTGAAA   1440
GGAGGGATGC  CTAAAAACGA  AGAACATTAA  AAACATATAT  TTGCACCGTC  TAATGGATTT   1500
ATGAAGCCGA  ATTC                                                         1514
```

( 2 ) INFORMATION FOR SEQ ID NO:22:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:22:

GAGACCCGGG AGCTTTCAGT GAAGTACGTG                  30

( 2 ) INFORMATION FOR SEQ ID NO:23:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:23:

CATAAATCCA TTAGACGGTG C                       21

( 2 ) INFORMATION FOR SEQ ID NO:24:

( i ) SEQUENCE CHARACTERISTICS:
  ( A ) LENGTH: 162 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:24:

ATCGATTGTT TGAGAAAAGA AGAAGACCAT AAAAATACCT TGTCTGTCAT CAGACAGGGT   60

ATTTTTTATG CTGTCCAGAC TGTCCGCTGT GTAAAAATAA GGAATAAAGG GGGGTTGTTA   120

TTATTTTACT GATATGTAAA ATATAATTTG TATAAGAAAA TG            162

( 2 ) INFORMATION FOR SEQ ID NO:25:

( i ) SEQUENCE CHARACTERISTICS:
  ( A ) LENGTH: 29 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:25:

GCATGCAATC GATTGTTTGA GAAAAGAAG                   29

( 2 ) INFORMATION FOR SEQ ID NO:26:

( i ) SEQUENCE CHARACTERISTICS:
  ( A ) LENGTH: 34 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:26:

CATTTTCTTA TACAAATTAT ATTTTACATA TCAG                34

( 2 ) INFORMATION FOR SEQ ID NO:27:

( i ) SEQUENCE CHARACTERISTICS:
  ( A ) LENGTH: 2017 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:27:

-continued

```
TGCGAAATCT ATCAAAAACT GAGAGTGAAT TCATTTTTTG ATAGAAAATT AAAACTATTC    60
AATATTTTGT CACAACCTGC TAGAATCCTA GGTAATAAGG GTCCCCTACA TATCTATCAT   120
TCATCACAAT GACCTTTGTT CATCTTGAAT TCTGAAGGGA GGATCGACCT GCTAATTTGT   180
CGTAAAAAAA TAGAAAATGG AGGAATGCTT TTATGAAGTT CAAAAAAATA GCCGCTCTAT   240
CCTTAGCAAC TTCCCTTGCT TTATTCCCTG CCTTCGGAGG TAGTTCACTG GCCAAGGAAG   300
CACCGAAACC GTTCCAACCT ATCAACAAAA CTTTGGATAA AGGCGCTTTC GAATCCGGTG   360
AAGTCATCGT CAATTCAAAG ATGGTGTATC CAAAAAGGCA CAAGGTTCTG CTCTGAACAA   420
AGCGGAGGCA AATGAACAGA AAGCATCAGC AAAAGATCCA TTTCAGGTAT TGGAAGTAGC   480
GGACGTCGAT CAAGCTGTTA AAGCACTGGA AAACAATCCG AATGTAGAAT ATGCTGAACC   540
AAACTATACC TTCCAAGCGA CTTGGTCACC GAATGACCCT TACTATTCTG CTTACCAGTA   600
TGGACCACAA AACACCTCAA CCCCTGCTGC CTGGGATGTA ACCCGTGGAA GCAGCACTCA   660
AACGGTGGCG GTCCTTGATT CCGGAGTGGA TTATAACCAC CCTGATCTTG CAAGAAAAGT   720
AATAAAAGGG TACGACTTTA TCGACAGGGA CAATAACCCA ATGGATCTTA ACGGACATGG   780
TACCCATGTT GCCGGTACTG TTGCTGCTGA TACGAACAAT GGAATTGGCG TAGCCGGTAT   840
GGCACCAGAT ACGAAGATCC TTGCCGTACG GGTCCTTGAT GCCAATGGAA GTGGCTCACT   900
TGACAGCATT GCCTCAGGTA TCCGCTATGC TGCTGATCAA GGGGCAAAGG TACTCAACCT   960
CTCCCTTGGT TGCGAATGCA ACTCCACAAC TCTTAAGAGT GCCGTCGACT ATGCATGGAA  1020
CAAAGGAGCT GTAGTCGTTG CTGCTGCAGG GAATGACAAT GTATCCCGTA CATTCCAACC  1080
AGCTTCTTAC CCTAATGCCA TTGCAGTAGG TGCCATTGAC TCCAATGATC GAAAAGCATC  1140
ATTCTCCAAT TACGGAACGT GGGTGGATGT CACTGCTCCA GGTGTGAACG AGGTTACTAG  1200
CTTTTCGTAG TAAGAGGTTA ATGCCTTGCA CCCACCTACA GTGACGAGGT CCACACTTGA  1260
TAGCATCAAC CGTTCCGAAT AATGGCTACT CCTACATGTC TGGTACGTCC ATGGCATCCC  1320
CTCACGTGGC CGGTTTGGCT GCTTTGTTGG CAAGTCAAGG TAAGAATAAC GTACAAATCC  1380
GCCAGGCCAT TGAGCAAACC GCCGATAAGA TCTCTGGCAC TGGAACAAAC TTCAAGTATG  1440
GTAAAATCAA CTCAAACAAA GCTGTAAGAT ACTAATAGAT AAAACAAGAG CACACCGTGA  1500
ATGGTGGGCT CTTTCATTAT GTTCACTACT GTTTACGAT CTGGCCGTTT TGGTTCAGGT  1560
AAACACTCTG GATGATGGTT CTATTAAACG GTTTCCCTTT ATAATCAGAC TTAATATCCG  1620
TTGTCAGGTT GTAGGTTCCT TCTCCTCCAT TGAACACTGT ACCACTCCCC TTGACAGACA  1680
ATTATAGGCA ACAGTCCAAC ATCCAAGGAA GAGGAGGTAA CTTGTGACAT GGTGAGGGA  1740
ACTGTCTGTG GGACAAAGGT TTCCCCTTAG GGTAGAACTC AAACTTGTGT GCTCGGTGAA  1800
CCCACTGACG ATACTTGACC CTGTTTCCAA AGGGGAATCC CATCTTGAGT TTGTAACACA  1860
CGAGCCACTT GGGTGACTGC TATGAACTAA CTTGCGACTG AGGGAAAGAG TCACCAGCGT  1920
GGTGGTTCAG TAGTAAGTTA CCTGAACACT TTGGTTCATT CAGTTTTGCC CCCAGGTTCT  1980
GGGAAAAAGG ATGAACTTCC ACTTCGGCCC TTTTTTT                           2017
```

NUCLEIC ACID CONSTRUCTS FOR THE PRODUCTION OF A BACILLUS ALKALINE PROTEASE

This application is a continuation-in-part of application Ser. No. 08/325,386, filed as PCT/DK93/00183, May 26, 1993, now U.S. Pat. No. 5,597,720, incorporated herein by reference.

1. TECHNICAL FIELD

The invention is directed to an isolated nucleic acid construct(s) comprising a nucleic acid sequence encoding a novel alkaline protease derived from a strain of *Bacillus sp.* Group I, as well as recombinant vectors and host cells comprising such constructs. Additionally, the invention is directed to a method for obtaining the protease. The invention is also directed to promoter and signal sequences derived from said alkaline protease as well as methods of using such promoter and signal sequences in the expression of heterologous nucleic acid sequences encoding heterologous proteins in bacteria.

2. BACKGROUND OF THE INVENTION

Detergent enzymes have been marketed for more than 20 years and are now well established as normal detergent ingredients in both powder and liquid detergents all over the world. With the trend towards lower washing temperature, detergent enzyme consumption has increased during late years. Enzymes used in washing formulations comprise proteases, lipases, amylases, cellulases, as well as other enzymes, or mixtures thereof. Commercially most important are proteases.

Detergent proteases have been developed by isolation of proteases found in nature followed by testing in detergent formulations. Most detergent proteases are obtained from members of the genus Bacillus. Currently, new types of proteases enter the market, offering the possibility of giving a better cost/performance ratio at various specified conditions.

Examples of commercial protease products are ALCALASE™, ESPERASE™ and SAVINASE™, all supplied by Novo Nordisk A/S, Denmark. These and similar enzyme products from other commercial sources are active in detergent solutions, i.e., at pH values in the range of from 8 to 11 and in the presence of sequestering agents, surfactants and bleaching agents such as sodium borate. The ALCALASE™ protease is produced by strains of the species *Bacillus licheniformis*. The ESPERASE™ and SAVINASE™ proteases are obtained by cultivation of strains of alkalophilic Bacilli.

It would be advantageous to provide novel alkaline proteases with a unique range of substrates, pH and/or temperature optima. It would also be advantageous to isolate novel proteases or produce proteases in high yield so that the proteases could be used in vitro. It would be advantageous to determine the amino acid and/or nucleic acid sequence of these proteases in order to determine, e.g., conserved and nonconserved regions and active sites, and thus, appropriate sites for mutagenesis to improve enzyme performance and to be able to produce the proteases using recombinant DNA technology.

By determining the nucleic acid sequence of the entire protease gene, one may determine the location of promoter and signal sequences. Such sequences may be of use in the expression of heterologous polypeptides.

3. SUMMARY OF THE INVENTION

The invention is related to a nucleic acid construct comprising a nucleic acid sequence encoding a protease having an apparent molecular weight of about 34 kD as determined by SDS-PAGE, a pI of approximately 9.3, a pH optimum in the range of about 9–11 determined at about 25° C. (with casein as substrate), a temperature optimum in the range of about 40°–55° C. determined at about pH 9.5 (with casein as substrate), and being obtainable from a strain of *Bacillus sp.* of group 1. *Bacillus sp.* of group 1 are most similar to *B. subtilis* and *B. firmus*. In a specific embodiment, the protease of the present invention is obtainable or derived from the PD498 strain, or from another host organism carrying the gene encoding a protease having immunochemical properties substantially identical or partially identical to those of the protease derived from *Bacillus sp.* PD498.

In one embodiment, the nucleic acid construct comprises the nucleic acid sequence encoding a protease having an amino acid sequence depicted in SEQ ID NO:1, which shows the sequence of the PD498 alkaline protease in its prepro form, SEQ ID NO:2, which shows the alkaline protease in its pro form or SEQ ID NO:3, which shows the PD498 alkaline protease in its mature form. In another embodiment, the nucleic acid construct comprises the nucleic acid sequence depicted in SEQ ID NO:4, which shows the entire nucleic acid sequence of the PD498 alkaline protease gene, which includes the coding region as well as the 5' and 3' flanking regions, SEQ ID NO:5, which shows the nucleic acid sequence encoding the PD498 alkaline protease in its prepro form, SEQ ID NO:6, which shows the nucleic acid sequence encoding the PD498 gene in its pro form, or SEQ ID NO:7, which shows the DNA sequence encoding the PD498 alkaline protease in its mature form.

In order to facilitate production of the novel protease, the invention also provides vectors, and recombinant host cells comprising the claimed nucleic acid construct, which vectors, constructs and recombinant host cells are useful in the recombinant production of the protease. Recombinant production of the protease of the invention is achieved by culturing a host cell transformed or transfected with the nucleic acid construct or vector of the invention, or progeny thereof, under conditions suitable for expression of the protease, and recovering the protease from the culture.

The invention is also directed to a promoter sequence derived from a gene encoding said novel protease or fragment thereof having substantially the same promoter activity as said sequence in which said promoter has the sequence shown in SEQ ID NO:8. The promoter may be used in the construction of a vector comprising said promoter sequence and a site for insertion into said vector of a heterologous DNA sequence. The term "heterologous" is intended to include a DNA sequence not expressed by the host cell in nature. Furthermore, the promoter may be used in a method for producing a heterologous protein comprising (a) transforming a bacterial cell, preferably a gram positive bacterium with said vector; (b) culturing the transformed cell of step (a); and (c) recovering said heterologous polypeptide from the tranformed cell of step (b).

The invention is also directed to a signal sequence derived from a gene encoding said novel protease or fragment thereof having substantially the same signal activity as said sequence in which said signal sequence has the amino acid sequence shown in SEQ ID NO:9. The signal sequence may be encoded by the DNA sequence shown in SEQ ID NO:10. The signal sequence may be used in the construction of a vector comprising (a) said signal sequence; (b) upstream from said signal sequence, a promoter sequence and a ribosome binding site sequence, transcription of said signal sequence being under the control of said promoter sequence; and (c) downstream from said signal sequence, a site for insertion into said vector of a heterologous DNA sequence, in the same reading frame as said signal sequence. Furthermore, the signal sequence may be used in a method for producing a heterologous protein comprising (a) transforming a bacterial cell, preferably a gram positive bacterium with said vector; (b) culturing the transformed cell of step (a); and (c) recovering said heterologous polypeptide from the tranformed cell of step (b).

The protease may be used in the washing process and therefore may be formulated into a detergent additive and/or composition.

4. BRIEF DESCRIPTION OF DRAWINGS

The present invention is further illustrated by reference to the accompanying drawings, in which.

FIGS. 3A–3I collectively show the complete amino acid and nucleotide sequence of the PD498 protease as well as associated upstream and downstream nucleotide sequences.

Figure 4:
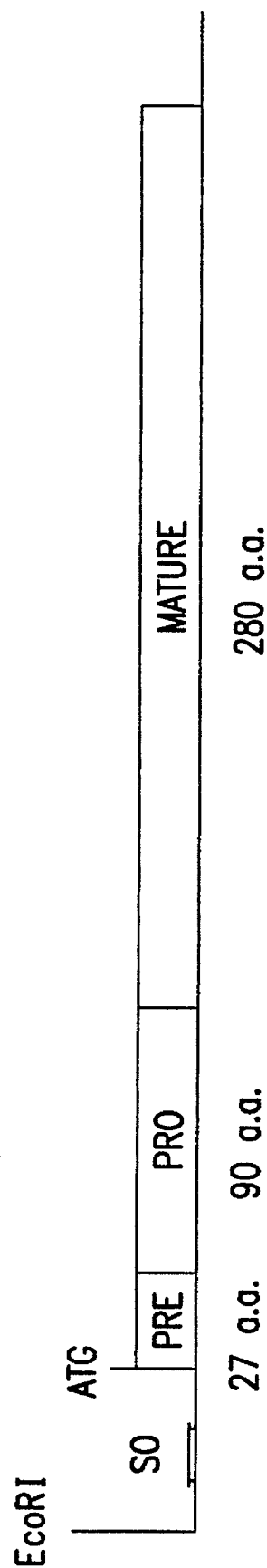

FIG. 4 shows the structure of PD498 protease.

Figure 5:
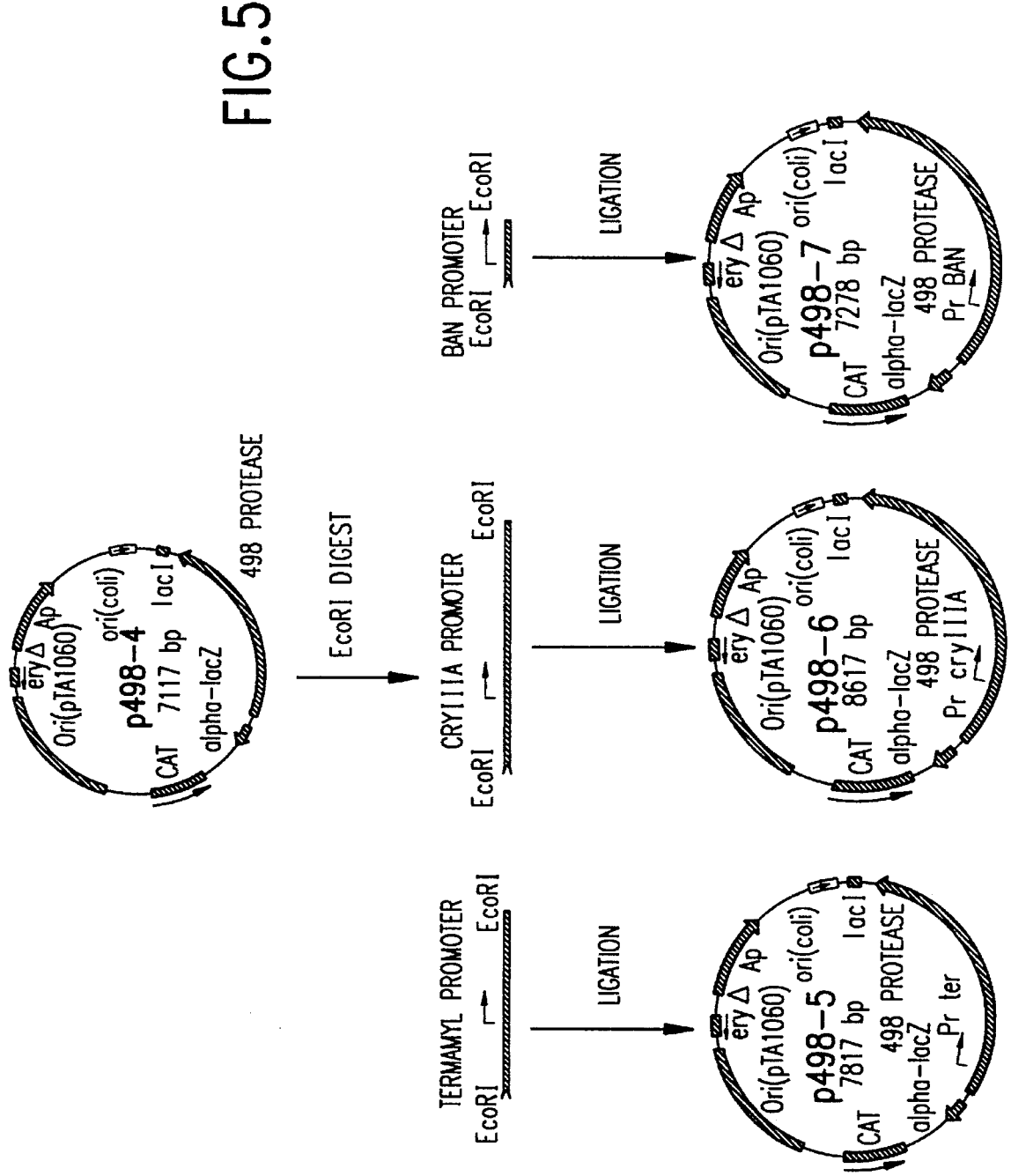

FIG. 5 shows the construction of promoter fusions.

Figure 6:
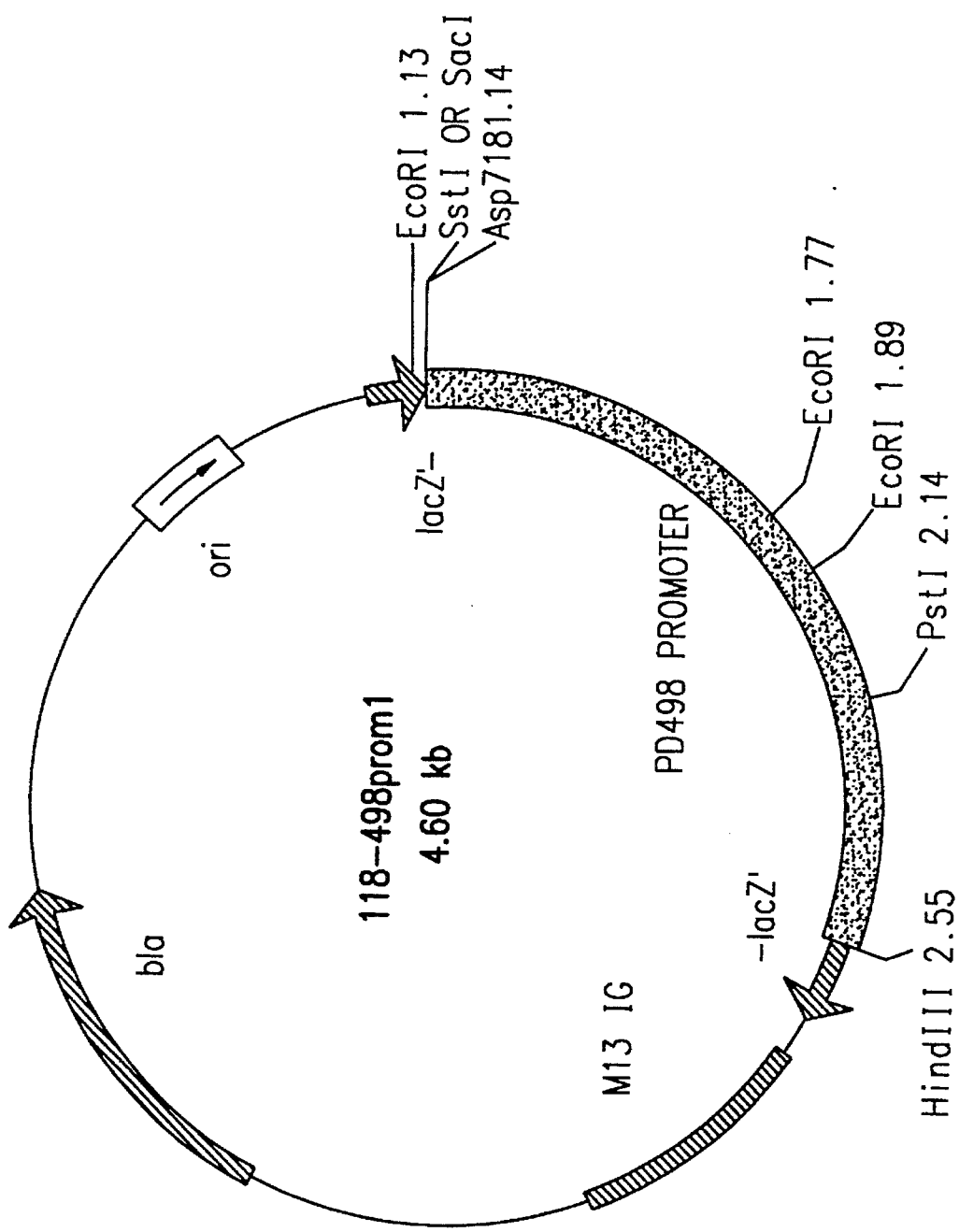

FIG. 6 shows a diagram of the plasmid p118-498prom1.

Figure 7:
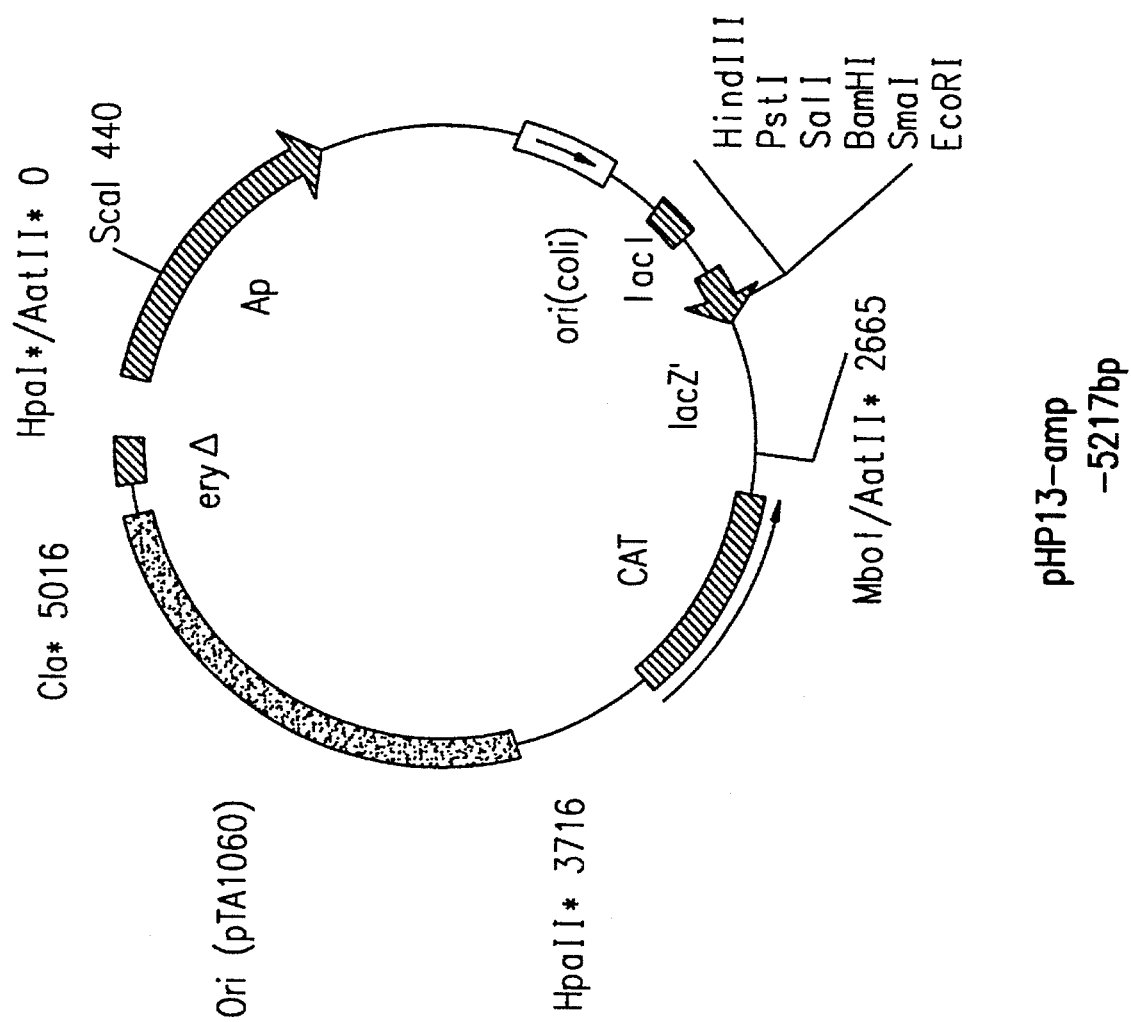

FIG. 7 shows a diagram of pHP13amp.

Figure 8:
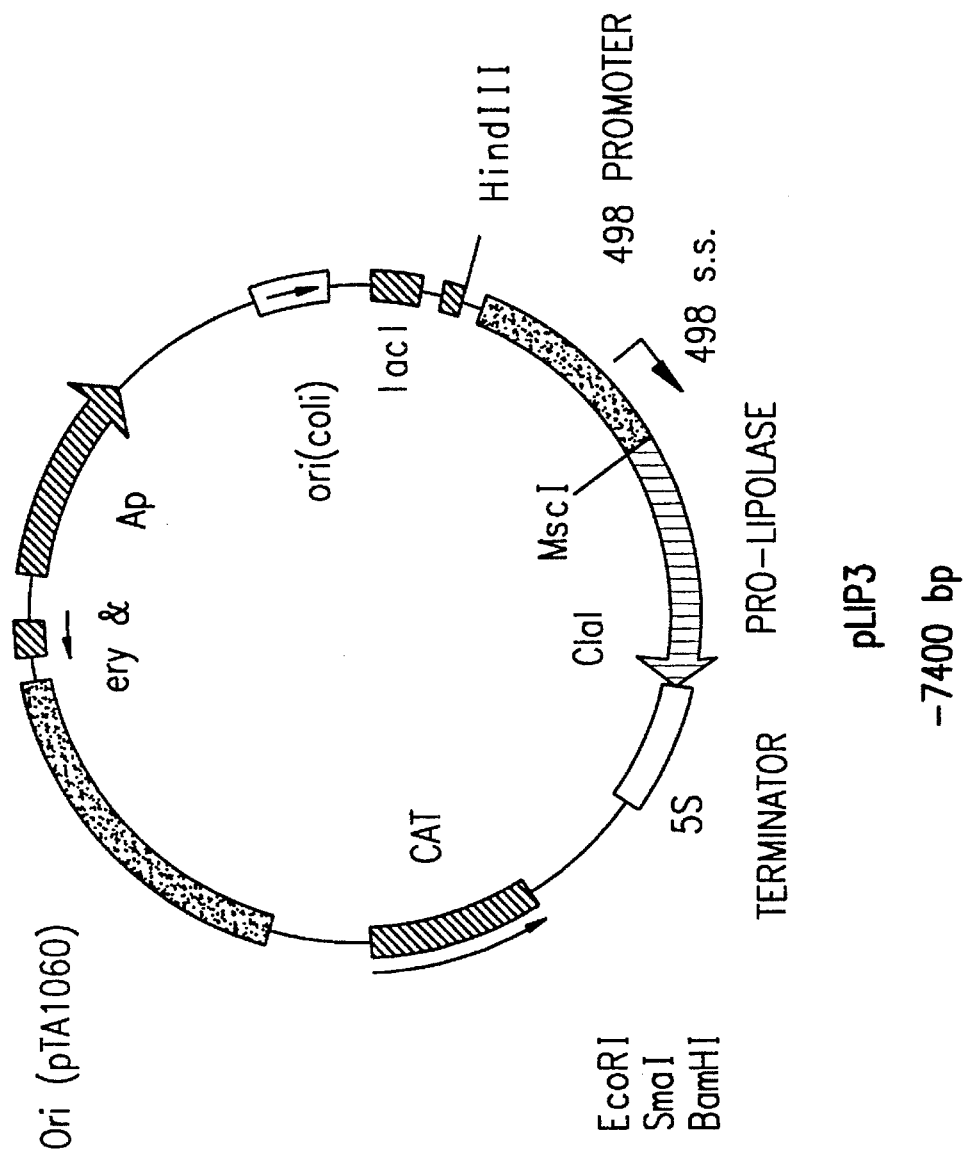

FIG. 8 shows a diagram of pLip3.

Figure 9:
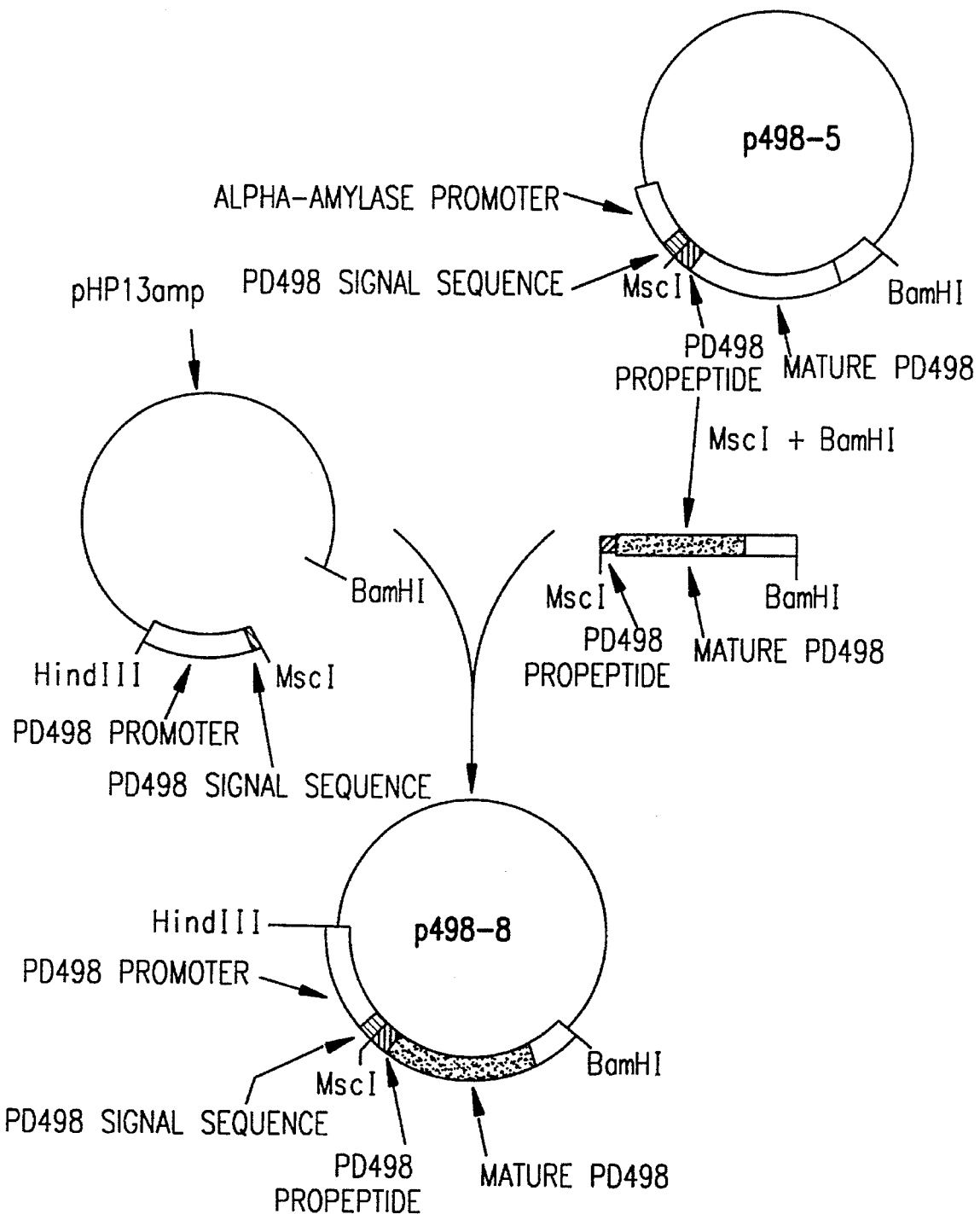

FIG. 9 shows the construction of p498-8.

Figure 10:
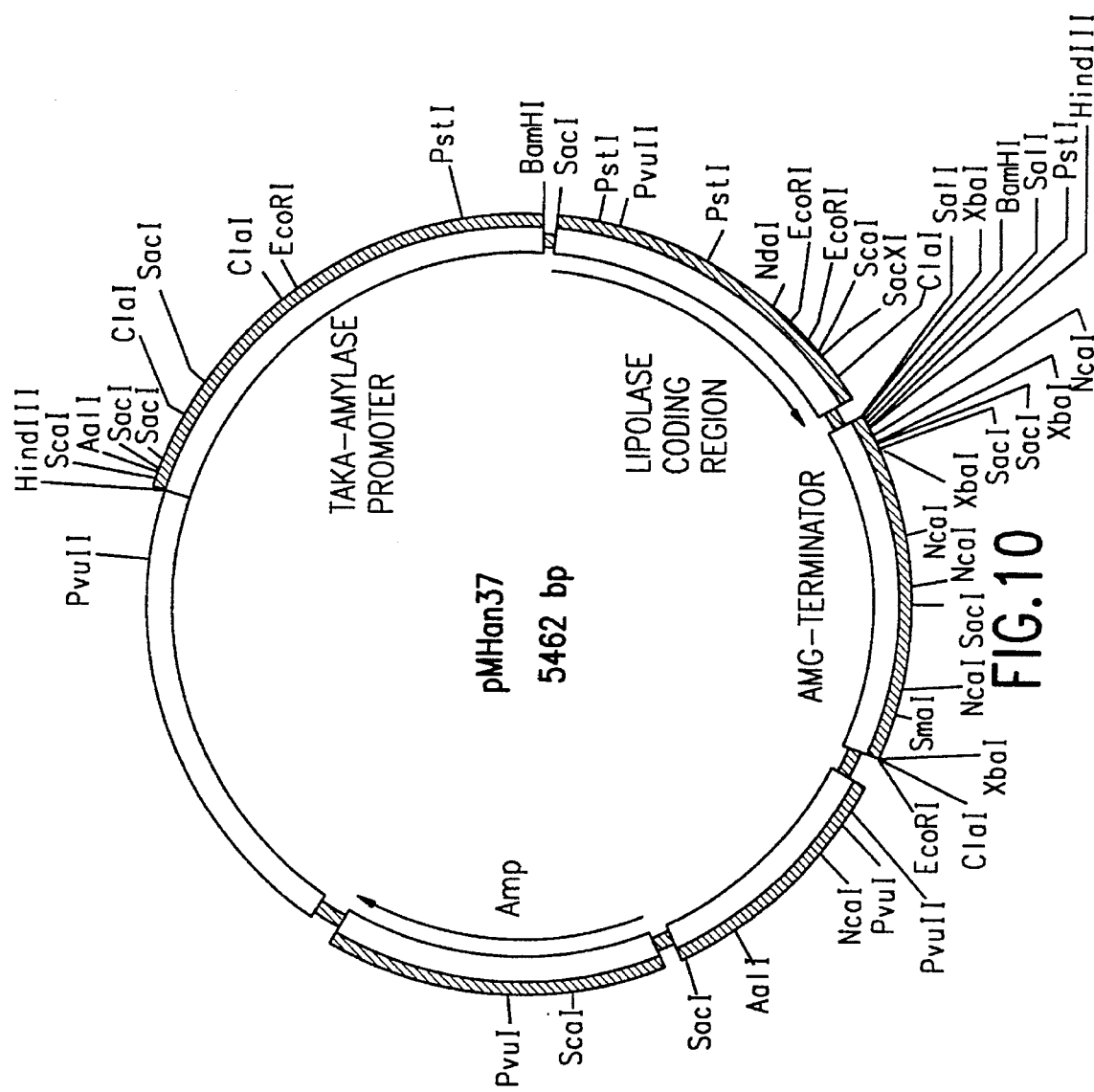

FIG. 10 shows a diagram of pMHan37.

Figure 11:
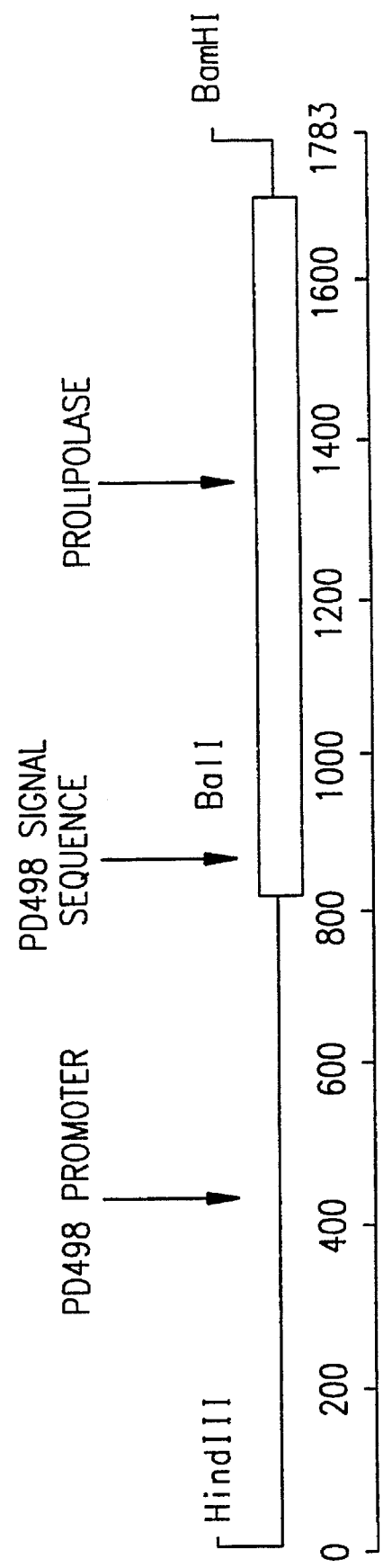

FIG. 11 shows a diagram of the PD498-lipolase fusion.

5. DETAILED DISCLOSURE OF THE INVENTION

5.1. Isolation of the Protease

5.1.1. The Microorganism

The microorganism which is able to produce said alkaline protease is isolated from a soil sample.

The microorganism is an aerobic, spore forming bacterium belonging to the genus Bacillus, group 1. In a preferred embodiment, morphologically it can be described as a motile rod with a diameter of 0.7–0.9 micron, and a length of 2–3 microns. The spores are round to ellipsoid, slightly swelling the sporangium, subterminal to terminal. Optimum temperature for growth is within 25°–37° C., and optimal pH for growth is within 7–9. No growth occurs at pH 9.7, nor at 50° C. The microorganism forms yellow colonies, round and smooth, on nutrient agar slants, and no diffusion of pigment into the agar is observed. In a specific embodiment, the microorganism is *Bacillus sp.* PD498 has been deposited according to the Budapest Treaty at NCIMB, under No. 40484.

5.1.2. Cultivation of the Microorganism

The microorganism which produces said alkaline protease can be cultivated under aerobic conditions in a nutrient medium containing assimilable carbon and nitrogen together with other essential nutrients, the medium being composed in accordance with the principles of the known art.

Suitable carbon sources are carbohydrates such as sucrose, glucose and starch, or carbohydrate containing materials such as cereal grain, malt, rice and sorghum. The carbohydrate concentration incorporated in the medium may vary widely, e.g., up to about 25% and down to about 1–5%, but usually about 8–10% will be suitable, the percentages being calculated as equivalents of glucose.

The nitrogen source in the nutrient medium may be of inorganic and/or organic nature. Suitable inorganic nitrogen sources are nitrates and ammonium salts. Among the organic nitrogen sources quite a number are used regularly in fermentation processes involving the cultivation of bacteria. Illustrative examples are soybean meal, cotton seed meal, peanut meal, casein, corn, corn steep liquor, yeast extract, urea, and albumin. In addition, the nutrient medium should also contain usual trace substances.

The microorganism is a strain of the Bacillus species. The Bacillus species is slightly alkalophilic. Therefore, the cultivation is preferably conducted at slightly alkaline pH values, which can be obtained by addition of suitable buffers such as sodium bicarbonate, about pH 9.0, after sterilization of the growth medium. For cultivation in tank fermentors, it is necessary to use artificial aeration. The rate of aeration is similar to that used in conventional tank fermentation.

After fermentation, liquid protease concentrates may be produced by removal of coarse material from the broth and, if desired, concentration of the broth by evaporation at low temperature or by ultrafiltration. Finally, preservatives may be added to the concentrate.

Solid protease preparations may be prepared from the purified and/or concentrated broth by precipitation with salts, such as $Na_2SO_4$ or water-miscible solvents, such as ethanol or acetone. Removal of the water in the broth by suitable drying methods, such as spray-drying, may also be employed.

5.1.3. Assay for Proteolytic Activity

The proteolytic activity may be determined with casein as substrate. One Casein Protease Unit (CPU) is defined as the amount of protease liberating about 1 μM of primary amino groups (determined by comparison with a serine standard) per minute under standard conditions, i.e., incubation for about 30 minutes at about 25° C. and about pH 9.5.

The proteolytic activity may also be determined by measuring the specific hydrolysis of succinyl-Ala-Ala-Pro-Leu-p-nitroanilide by said protease. The substrate is initially dissolved in for example, DMSO and then diluted about 50 fold in about 0.035M borate buffer, about pH 9.45. All protease samples may be diluted about 5–10 fold by the same borate buffer. Equal volumes of the substrate solution and sample are mixed in a well of an ELISA reader plate and read at about 405 nm at 25° C. All sample activities and concentrations are normalized to the standard protease solution activity and concentration, respectively.

5.2. The Protease

Said protease can be described by the following characteristics.

5.2.1. Physical-Chemical Properties

The protease of the invention has an apparent molecular weight of about 34 kD when determined by SDS-PAGE. A pI of approximately 9.3 is determined by isoelectric focusing on LKB Ampholine® PAG plates. The protease activity is inhibited by PMSF, a serine proteinase inhibitor. EDTA and soybean-protease inhibitor do not influence the protease activity.

Figure 1:
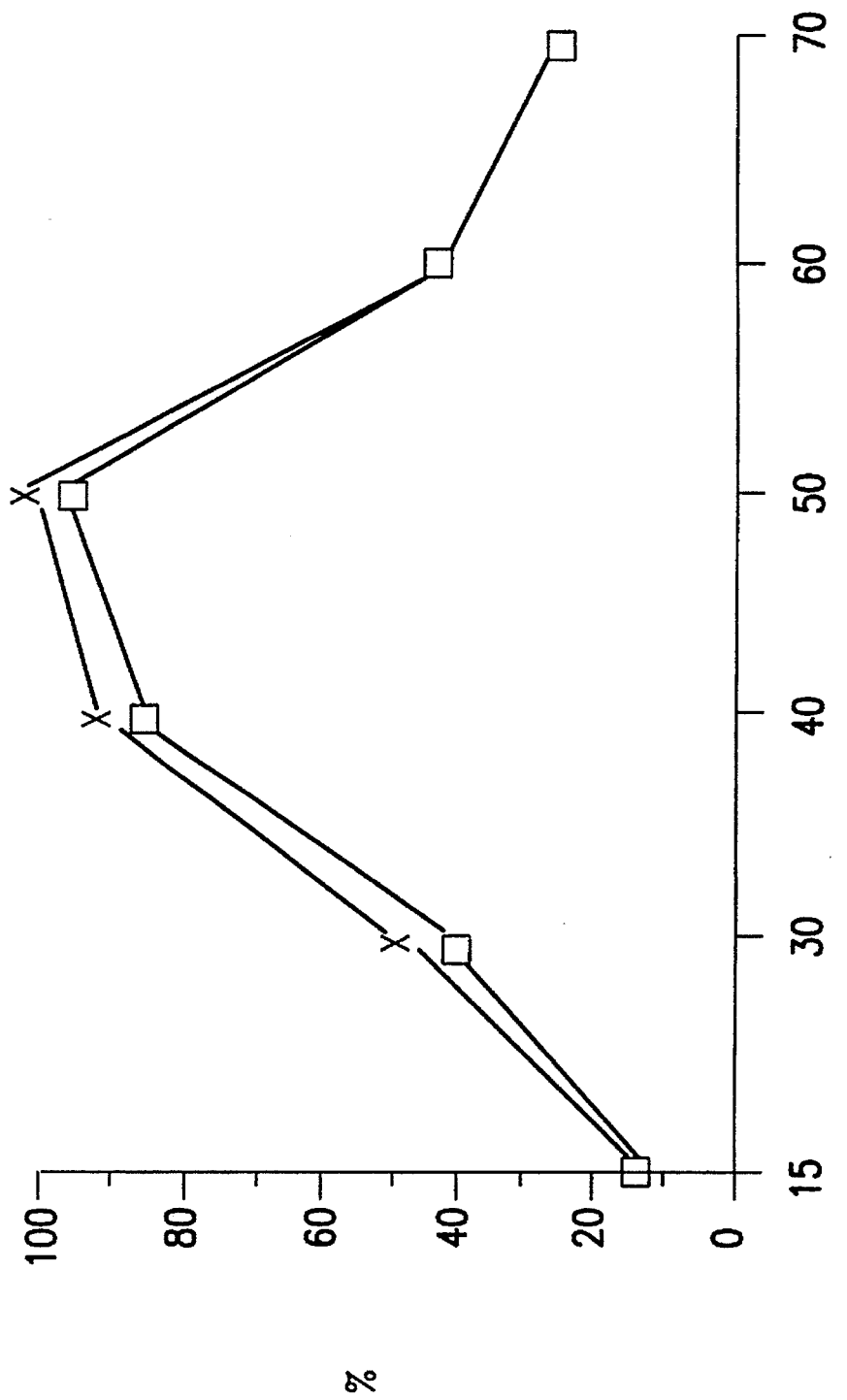
FIG. 1 shows shows the relation between temperature and the proteolytic activity of the PD498 alkaline protease with 2% casein as substrate, determined at pH 9.5; Buffer, Buffer+0.1% STPP (sodium tripolyphosphate).

The temperature-activity relationship is presented in FIG. 1. The activity is determined with 2% casein as substrate at about pH 9.5 in the presence (white squares) and absence (black squares) of 0.1% sodium tripolyphosphate (STPP, a common ingredient in many commercial detergents). The assay for proteolytic activity described previously is used with the modification that the incubation temperature is varied in the interval of from about 15° to about 70° C. It appears from the figure that the protease possesses proteolytic activity from about 15° C. to about 70° C., and has a temperature optimum in the range of from about 40°–55° C.

Figure 2:
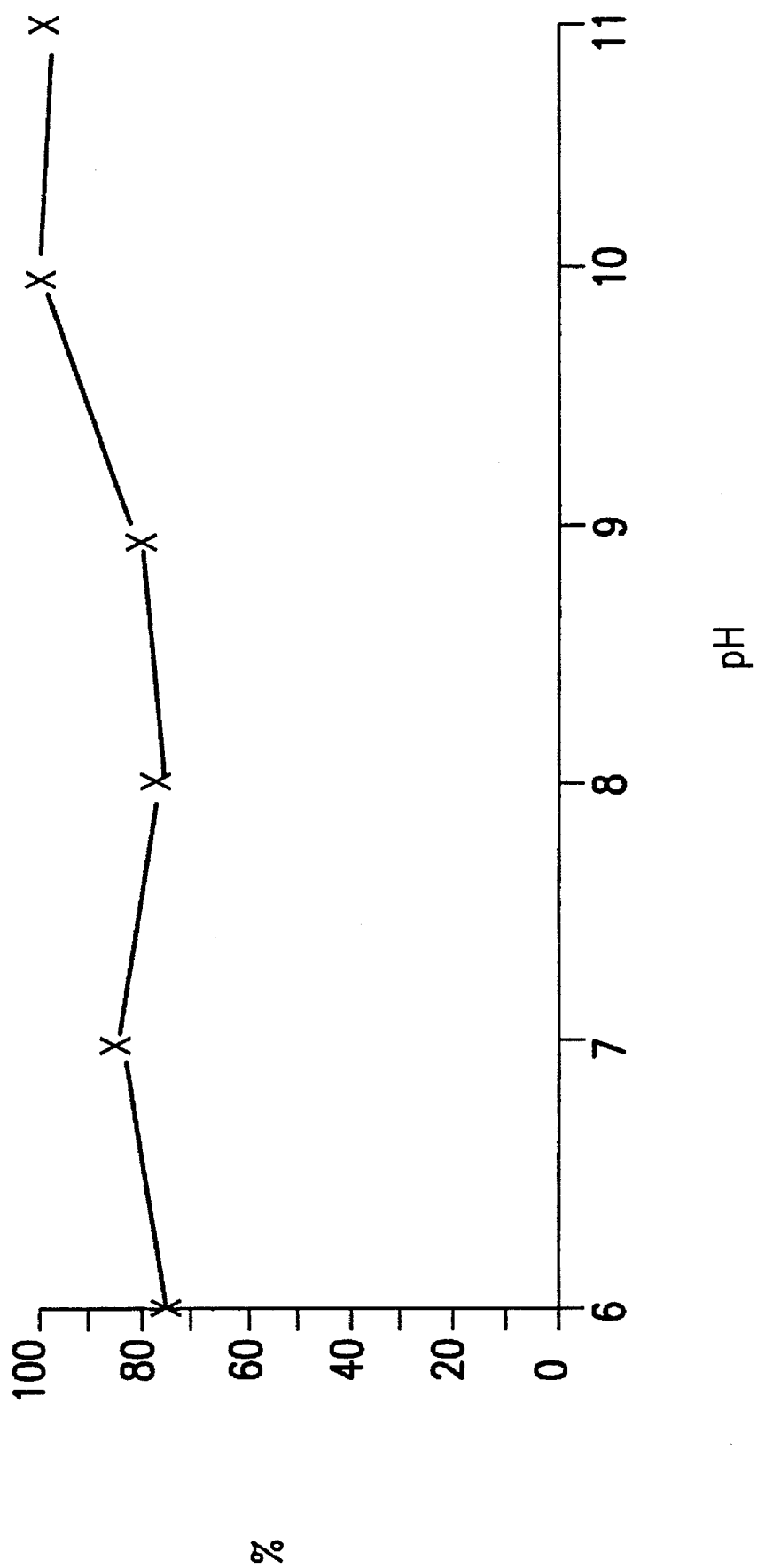
FIG. 2 shows the relation between pH and the proteolytic activity of the PD498 alkaline protease with 1% casein as substrate, determined at 25° C.
Figure 3C:
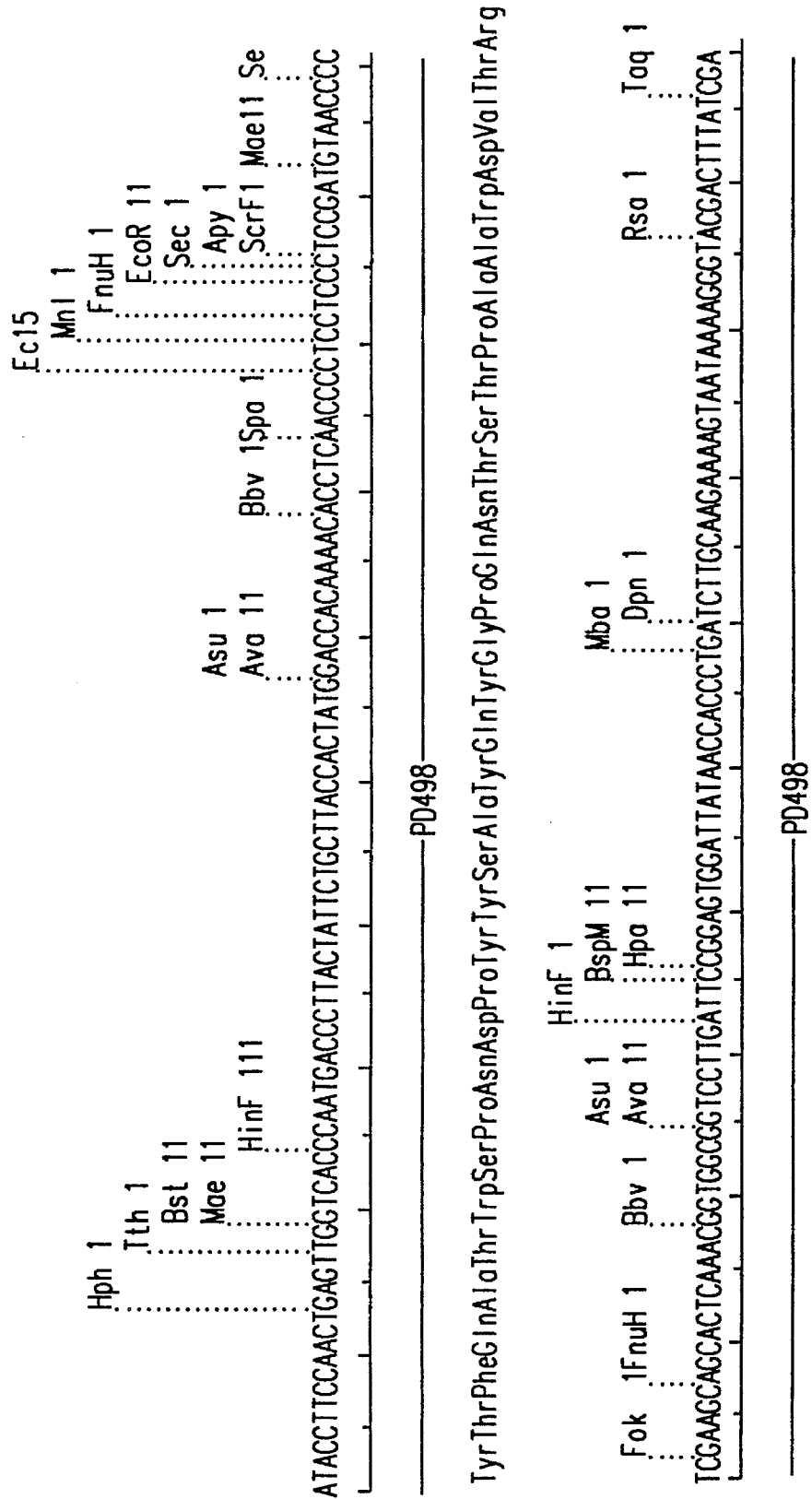
Figure 3D:
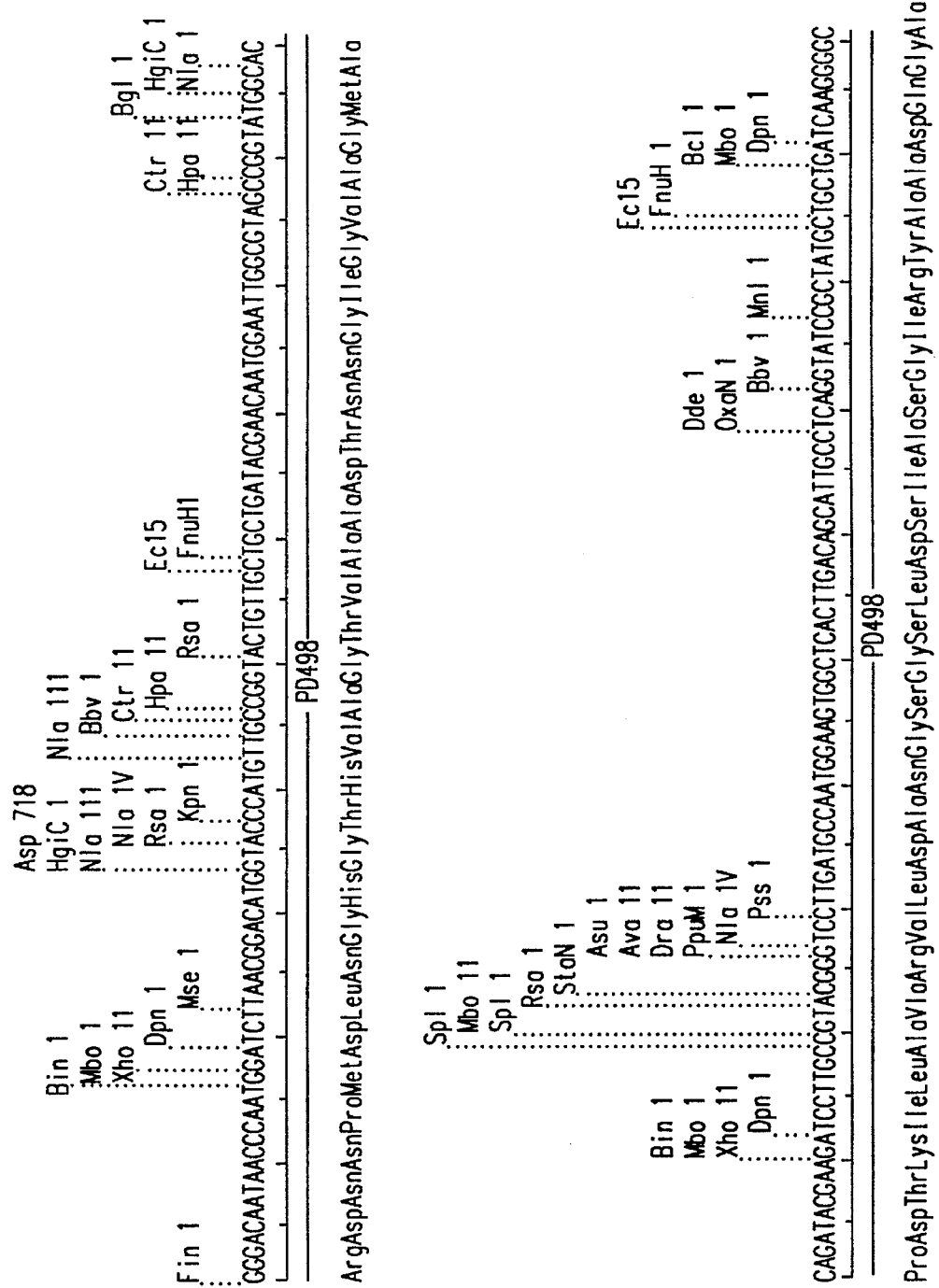
Figure 3H:
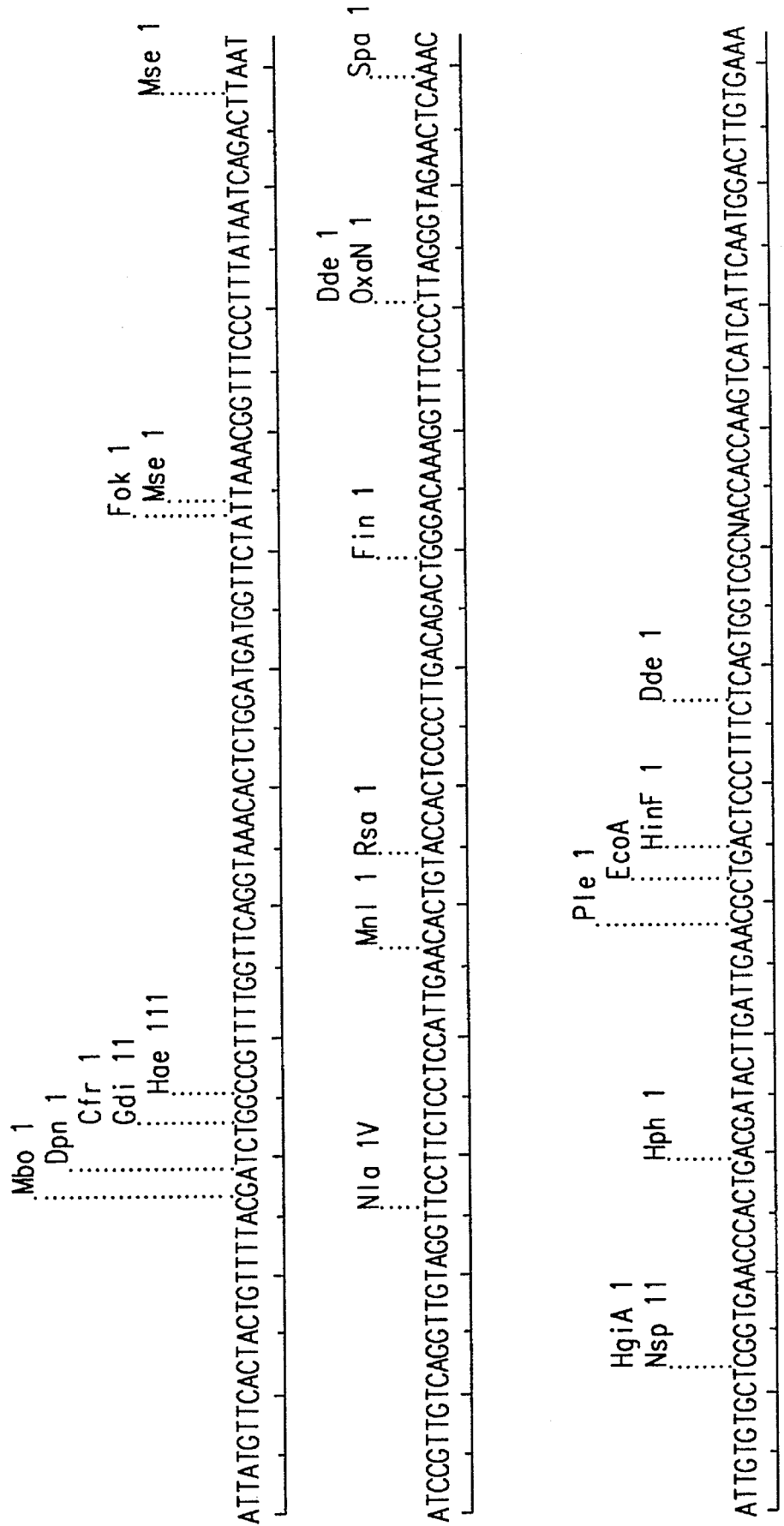
Figure 31:
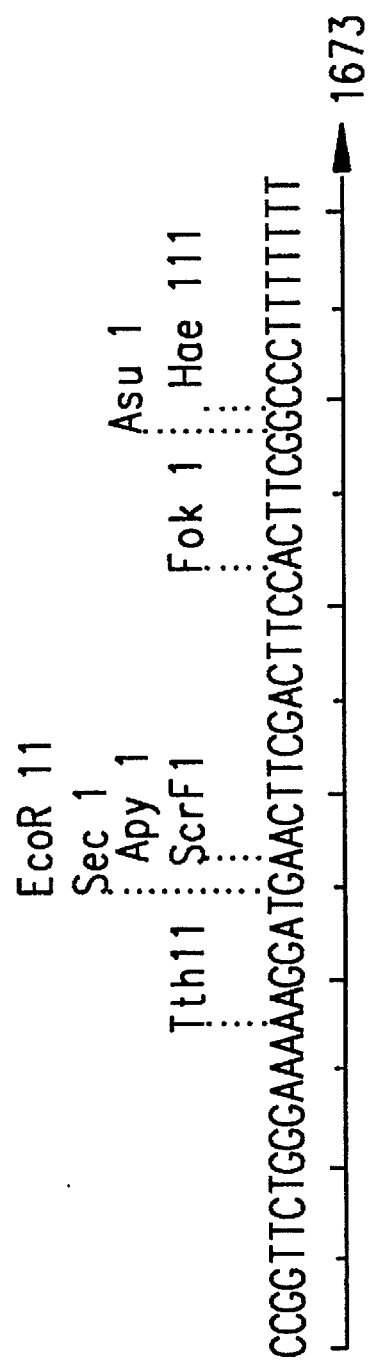

The dependence of activity on pH is determined by the same procedure, using buffers adjusted to predetermined pH values in the pH range of from about 6 to 11. The result is shown in FIG. 2. It appears from this figure that the protease possesses proteolytic activity in a very broad pH range of from below about pH 6 to above about pH 11, with an apparent pH optimum in the range of from about pH 9–11.

Furthermore, it is found that the protease of the invention is stable for about 60 minutes at about 25° C. under washing conditions when determined in European type and American type detergents.

5.2.2. Immunochemical Properties

Said protease has immunochemical properties substantially identical or at least partially identical to those of a protease derived from the strain *Bacillus sp.* PD498, NCIMB No. 40484.

The immunochemical properties can be determined immunologically by cross-reaction identity tests. The identity tests can be performed by the well-known Ouchterlony double immunodiffusion procedure or by tandem crossed immunoelectrophoresis according to N. H. Axelsen; Handbook of Immunoprecipitation-in-Gel Techniques; Blackwell Scientific Publications (1983), chapters 5 and 14. The terms "antigenic identity" and "partial antigenic identity" are described in the same book, Chapters 5, 19 and 20.

Monospecific antiserum is generated according to the above mentioned method by immunizing rabbits with the purified protease of the invention. The immunogen is mixed with Freund's adjuvant and injected subcutaneously into rabbits every second week. Antiserum is obtained after a total immunization period of 8 weeks, and immunoglobulin is prepared therefrom as described by N. H. Axelsen, supra.

Ouchterlony double immunodiffusion tests show no cross reaction between the protease of the invention and the known alkaline serine proteases from Bacillus species, e.g., ALCALASE™, SAVINASE™, ESPERASE™, subtilisin Novo (available from Novo Nordisk A/S, Denmark), and KAZUSASE™ (available from SHOWA DENKO, Japan).

5.3. Nucleic Acid Construct

As used herein the term "nucleic acid construct" is intended to indicate any nucleic acid molecule of genomic DNA, synthetic DNA or RNA origin. The term "construct" is intended to indicate a nucleic acid segment which may be single- or double-stranded, and which may be based on a complete or partial naturally-occurring nucleotide sequence encoding the protease. The construct may optionally contain other nucleic acid segments.

The nucleic acid construct of the invention encoding said protease may suitably be of genomic origin, for instance obtained by preparing a genomic library and screening for DNA sequences coding for all or part of the protease by hybridization using synthetic oligonucleotide probes in accordance with standard techniques (cf. Sambrook et al., Molecular Cloning, A Laboratory Mannual, Cold Spring Harbor Laboratory, Cold Spring Harbor, N.Y., 1989). For the present purpose, the DNA sequence encoding the protease is obtainable by isolating chromosomal DNA from the strain of *Bacillus sp.* described in Section 5.1, supra and screening a genomic DNA library.

The nucleic acid construct of the invention encoding the protease may also be prepared synthetically by established standard methods, e.g., the phosphoramidite method described by Beaucage and Caruthers, *Tetrahedron Letters* 22 (1981), 1859–1869, or the method described by Matthes et al., *EMBO Journal* 3 (1984), 801–805. According to the phosphoramidite method, oligonucleotides are synthesized, e.g., in an automatic DNA synthesizer, purified, annealed, ligated and cloned in suitable vectors.

Furthermore, the nucleic acid construct may be of mixed synthetic and genomic origin and may be prepared by ligating fragments of synthetic or genomic DNA (as appropriate), the fragments corresponding to various parts of the entire nucleic acid construct, in accordance with standard techniques.

The nucleic acid construct may also be prepared by polymerase chain reaction using specific primers, for instance as described in U.S. Pat. No. 4,683,202 or Saiki et al., Science 239 (1988), 487–491.

In a currently preferred embodiment, the nucleic acid construct of the invention comprises the DNA sequence shown in SEQ ID NO:4 as well as nucleic acid sequences encoding the amino acid sequence shown in SEQ ID NO:1, SEQ ID NO:2 or SEQ ID NO:3, e.g., DNA sequences depicted in SEQ ID NO:5, SEQ ID NO:6, or SEQ ID NO:7, respectively. The invention further encompasses nucleic acid sequences which hybridize to a nucleic acid molecule (either genomic or synthetic) encoding the amino acid sequence shown in SEQ ID NO:1, SEQ ID NO:2 or SEQ ID NO:3 under the following conditions:presoaking in 5X SSC and prehybridizing for 1 hr. at about 40° C. in a solution of 20% formamide, 50 mM sodium phosphate, pH 6.8, and 50 μg denatured sonicated calf thymus DNA, followed by hybridization at about 40° C. for 18 hrs. in the same solution, followed by a wash in 0.4X SSC at a temperature of about 45° C.

Useful variants within the categories defined above include, for example, ones in which the DNA encodes changes in which conservative amino acid substitutions have been made, which substitutions do not significantly affect the activity of the protein. By conservative substitution is meant that amino acids of the same class may be substituted by any other of that class. For example, the nonpolar aliphatic residues, Ala, Val, Leu, and Ile may be interchanged, as may be the basic residues Lys and Arg, or the acidic residues Asp and Glu. Similarly, Ser and Thr are conservative substitutions for each other, as are Asn and Gln. It will be apparent to the skilled artisan that such substitutions can be made outside the regions critical to the function of the molecule and still result in an active protease. Retention of the desired activity can readily be determined by using the assay procedures described above.

The nucleic acid construct is preferably a DNA construct which term will be used exclusively in the following.

5.4. Recombinant Vector

In a further aspect, the present invention relates to a recombinant vector comprising a DNA construct of the invention. The recombinant vector into which the DNA construct of the invention is inserted may be any vector which may conveniently be subjected to recombinant DNA procedures, and the choice of vector will often depend on the host cell into which it is to be introduced. Thus, the vector may be an autonomously replicating vector, i.e., a vector which exists as an extrachromosomal entity, the replication of which is independent of chromosomal replication, e.g., a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the protease of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g., transcription initiates in a promoter and proceeds through the DNA sequence coding for the protease of the present invention.

The promoter may be any DNA sequence which shows transcriptional activity in the host cell of choice and may be derived from genes encoding proteins either homologous or heterologous to the host cell. Specifically, examples of suitable promoters for use in bacterial host cells include but are not limited to the promoter of the *Bacillus stearothermophilus* maltogenic amylase gene, the the *Bacillus amyloliquefaciens* (BAN) amylase gene, the *Bacillus subtilis* alkaline protease gene, the *Bacillus pumilus* xylosidase gene, the *Bacillus thuringiensis* cryIIIA or the *Bacillus licheniformis* alpha-amylase gene. Other promoters that may be used include but are not limited to phage Lambda $P_R$ or $P_L$ promoters or the *E. coli* lac, trp or tac promoters.

The promoter may also be derived from a gene encoding said protease or a fragment thereof having substantially the same promoter activity as said sequence. The sequence of the promoter is shown in SEQ ID NO:8. The invention further encompasses nucleic acid sequences which hybridize to the promoter sequence shown in SEQ ID NO:8 under the following conditions:presoaking in 5X SSC and prehybridizing for 1 hr. at about 40° C. in a solution of 20% formamide, 50 mM sodium phosphate, pH 6.8, and 50 μg denatured sonicated calf thymus DNA, followed by hybridization in the same solution for 18 hrs. at about 40° C., followed by a wash in 0.4X SSC at a temperature of about 45° C., or which have at least about 90% homology and preferably about 95% homology to SEQ ID NO:8, but which have substantially the same promoter activity as said sequence. This promoter may be used to promote the expression of either said protease or a heterologous DNA sequence, e.g. lipolase®, a 1,3-specific lipase, hereinafter referred to as Lipolase®. The enzyme may be encoded by the DNA sequence shown in SEQ ID NO:11 and may have an amino acid sequence shown in SEQ ID NO:12. The enzyme may also be a Lipolase® variant, e.g., D96L, E210K, E210L (see WO 92/05249).

The recombinant vector of the invention may further comprise a DNA sequence enabling the vector to replicate in the host cell in question. When the host cell is a bacterial cell, sequences enabling the vector to replicate are various ori sequences.

The vector may also comprise a selectable marker, e.g., a gene the product of which which confers resistance to a drug, e.g., ampicillin, kanamycin, tetracycline, chloramphenicol, neomycin, hygromycin or methotrexate.

To direct a protease of the present invention into the secretory pathway of the host cells, a secretory signal sequence (also known as a leader sequence or pre sequence) may be provided in the recombinant vector. The secretory signal sequence is joined to the DNA sequence encoding the pro immature protease in the correct reading frame (see, for example, FIG. 4). A pro sequence is an amino acid sequence between the pre sequence and mature protease that is necessary for the secretion of the protease. Cleavage of the pro sequence will result in a mature active protease. Secretory signal sequences are commonly positioned 5' to the DNA sequence encoding the protease. The secretory signal sequence may be that normally associated with the protease or may be from a gene encoding another secreted protein.

For secretion from bacterial cells, the signal peptide may be a naturally occurring signal peptide, or a functional part thereof, or it may be a synthetic peptide. Suitable signal peptides include but are not limited to sequences derived from *Bacillus licheniformis* alpha-amylase, *Bacillus lentus* alkaline protease, and *Bacillus amyloliquefaciens* amylase.

For secretion from bacterial cells, the signal peptide may also be the signal peptide from the protease disclosed in the instant application. The amino acid sequence of the signal sequence is shown in SEQ ID NO:9. The signal sequence may be encoded by a nucleic acid sequence depicted in SEQ ID NO:10. The invention further encompasses nucleic acid sequences which hybridize to the nucleic acid sequence shown in SEQ ID NO:10 under the following conditions:presoaking in 5X SSC and prehybridizing for 1 hr. at about 40° C. in a solution of 20% formamide, 50 mM sodium phosphate, pH 6.8, and 50 μg denatured sonicated calf thymus DNA, followed by hybridization in the same solution for 18 hrs. at about 40° C., followed by a wash in 0.4X SSC at a temperature of about 45° C., or which have at least about 90% homology and preferably about 95% homology to SEQ ID NO:5, but which have substantially the same signal activity as said sequence. This signal may be used to facilitate the secretion of either said protease or a heterologous DNA sequence, e.g. lipolase®, a 1,3-specific lipase, hereinafter referred to as Lipolase®. The enzyme may be encoded by the DNA sequence shown in SEQ ID NO:11 and may have an amino acid sequence shown in SEQ ID NO:12. The enzyme may also be a Lipolase® variant, e.g., D96L, E210K, E210L (see WO 92/05249).

The procedures used to ligate the DNA sequences coding for the present protease, the promoter and/or secretory signal sequence, respectively, and to insert them into suitable vectors containing the information necessary for replication, are well known to persons skilled in the art (cf., for instance, Sambrook et al., op. cit.).

5.5. Host cells

The DNA sequence encoding the present alkaline protease introduced into the host cell may be either homologous or heterologous to the host in question. If homologous to the host cell, i.e., produced by the host cell in nature, it may be operably connected to another promoter sequence or, if applicable, another secretory signal sequence and/or terminator sequence than in its natural environment. The term "homologous" is intended to include a nucleic acid sequence encoding a protease native to the host organism in question; the nucleic acid acid sequence may be introduced into the host organism in multicopy form. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell which is capable of producing the present alkaline protease and includes but is not limited to bacteria, yeast, fungi and higher eukaryotic cells.

Examples of bacterial host cells which, on cultivation, are capable of producing and secreting the protease of the invention are gram positive bacteria such as strains of Bacillus, such as strains of *B. subtilis, B. licheniformis, B. lentus, B. brevis, B. stearothermophilus, B. alkalophilus, B. amyloliquefaciens, B. coagulans, B. circulans, B. lautus, B. megatherium* or *B. thuringiensis*, or gram negative bacteria such as *Escherichia coli*. The transformation of the bacteria may be effected by protoplast transformation or by using competent cells in a manner known per se (cf. Sambrook et al., supra).

When expressing the protease in bacteria such as *E. coli*, the protease may be retained in the cytoplasm, typically as insoluble granules (known as inclusion bodies), or may be directed to the periplasmic space by a bacterial secretion sequence. In the former case, the cells are lysed and the granules are recovered and denatured after which the protease is refolded by diluting the denaturing agent. In the later case, the protease may be recovered from the periplasmic space by disrupting the cells, e.g., by sonication or osmotic shock, to release the contents of the periplasmic space and recovering the protease.

The transformed host cell described above is then cultured in a suitable nutrient medium under conditions permitting the expression of the present protease, after which the resulting protease is recovered from the culture. The medium used to culture the cells may be any conventional medium suitable for growing the host cells, such as minimal or complex media containing appropriate supplements. Suitable media are available from commercial suppliers or may be prepared according to published recipes (e.g., in catalogues of the American Type Culture Collection). The protease produced by the cells may then be recovered from the culture medium by conventional procedures including separating the host cells from the medium by centrifugation or filtration, precipitating the proteinaceous components of the supernatant or filtrate by means of a salt, e.g., ammonium sulphate, purification by a variety of chromatographic procedures, e.g., ion exchange chromatography, gel filtration chromatography, affinity chromatography, or the like, dependent on the type of protease in question.

The invention is further illustrated in the following examples, which are not intended to be in any way limiting to the scope of the invention as claimed.

6. EXAMPLES

6.1. Isolation of PD498 Protease

*Bacillus sp.* PD498 is cultivated at 25° C. on a rotary shaking table (300 r.p.m.) in 500 ml baffled Erlenmeyer flasks containing 100 ml of medium of the following composition (per liter):

| | |
|---|---|
| Potato starch | 100 g |
| Ground barley | 50 g |
| Soybean flour | 20 g |
| $Na_2HPO_4 \times 12\ H_2O$ | 9 g |
| Pluronic 54R (BASF) | 0.1 g |
| Sodium caseinate | 10 g |

The starch in the medium is liquified with alpha-amylase, and the medium is sterilized by heating at 120° C. for 45 minutes.

After sterilization, the pH of the medium is adjusted to 9.0 by addition of 10 ml of a 1M solution of sodium bicarbonate.

After 4 days of incubation, the proteolytic activity of the culture is determined using the method described above. The protease activity of the broth is 5 CPU/l.

After separation of the solid material the protease is purified by a conventional chromatographic method. Yield from 3.5 l of culture broth is 31 ml with 120 CPU/l. Purity is more than 90% as judged by both SDS-PAGE and isoelectric focusing.

The characteristics of the preparation prepared in accordance with this Example have been referred to earlier in this specification, and reference is made hereto.

6.2. Cloning and Expression of PD498 Protease 6.2.1. Materials and Methods
  6.2.1.1. Strains
  *Escherichia coli* DH5 F-Φ80dlacZΔM15Δ(lacZYA-argF) U169 deoR recA1 endA1 hsdR17($r_{K-}$,$m_{K+}$)supE44-thi-1 gyrA96 relA1 (BRL) is used for all *E. coli* transformations according to manufacturer's specifications (BRL). A *B. subtilis* protease deficient strain is made competent by the procedure of Anagnostopolis and Spizizen (*J. Bacteriol.* 81: 741–746, 1961).

6.2.1.2. DNA Isolation and Gene Library Construction
  PD498 chromosomal DNA is isolated as described by Pitcher, et. al.(*Letters in Applied Micro.* 8: 151–156, 1989). 100 μg of DNA is digested with EcoR1 and run on an agarose gel. DNA of 5–8 kb is isolated using the Qiaex system (Qiagen). This DNA is ligated to EcoR1-cut, CIP (calf intestinal phosphatase) treated puC19 (BRL) at a ratio of 4:1 respectively. The ligation mix is then transformed into *E. coli* strain DH5alpha (BRL).

6.2.1.3. PCR Amplification of the 180 bp Fragment
  The amplification of a 180 bp fragment of the protease gene is performed using two mixed primers, group A and B, based on partial amino acid sequence of the protease. The letter amino acid sequences are Sequence A: AYQYGPQNT (SEQ ID NO:13) and sequence B: YDFIDYDNNPMD (SEQ ID NO:14). The primers and total PD498 DNA are used in a reaction of 95° C./5 minutes followed by 30 cycles of 95° C./1 minute, 55° C./1 minute, 72° C./1 minute in an Ericomp PCR machine.

Primer group A: GCNTAYCARTAYGGNCCNCAR-AAYAC (SEQ ID NO:15)
  Primer group B: TCCATNGGRTTRTTRTCRTARTC-DATRAARTCRTA (SEQ ID NO:16)

6.2.1.4. Subcloning of PCR Reaction Product
  The PCR product is cloned for sequencing using the TA Cloning vector pCRII (Invitrogen, San Diego, Calif.) following manufacturer's specifications. The insert DNA is DIG (digoxigenin)-labeled and Southern hybridizations and colony blots are performed using the Genius system from Boehringer Mannheim as modified by Engler-Blum (1993, *Anal. Biochemistry* 210:235–244).

6.2.1.5. DNA Sequencing
  DNA sequences are determined using Taq polymerase cycle-sequencing with fluorescent labeled dideoxynucleotides. The sequencing reactions are run on an Applied Biosystems automatic DNA sequencer (Model 373A, version 1.2.0).

6.2.1.6. Construction of Vector Containing PD498 Protease Driven By the amyL Promoter The alpha-amylase (amyL) promoter (SEQ ID NO:17), an "up" mutant promoter from *Bacillus licheniformis*, is obtained by PCR amplification from *B. licheniformis* DNA using the following primers:
5'-AAGGCATGCGTCCTTC-3' (SEQ ID NO:18)
5'-CTTTCAATGTGTAACATA-3' (SEQ ID NO:19)
The resulting 630 bp fragment is cloned into the pCRII vector (Invitrogen), enabling the cloned fragment to be easily isolated as an EcoRI fragment.

The protease gene is subcloned as a 1.9 kb EcoRI-EcoRV fragment into EcoRI, SmaI-cut pUC19, then removed as a 1.9 kb EcoRI-HindIII fragment and cloned into EcoRI-HindIII-cut pHP13amp, an *E. coli-B. subtilis* shuttle vector (FIG. 8). The resulting plasmid, p498-4, is digested with EcoRI, treated with calf intestinal phosphatase (CIP), and ligated to the amyL promoter fragment described above, generating plasmid p498-5 (FIG. 5). *B. subtilis* colonies containing the promoter in the correct orientation relative to the PD498 coding region are selected by their ability to form halos on agar plates containing the appropriate antibiotic and 1% milk.

6.2.1.7. Construction of Vector Containing PD498 Protease Driven By cryIIIA Promoter The cryIIIA promoter (SEQ ID NO:20) from *Bacillus thuringiensis* var. *tenebrionis* is amplified by PCR using the following primers:
5'-GAGACCCGGGAGCTTTCAGTGAAGTACGTG-3' (SEQ ID NO:21)
5'-CATAAATCCATTAGACGGTGC-3' (SEQ ID NO:22)
The resulting 1500 bp fragment is again cloned into the pCRII vector (Invitrogen), removed as an EcoRI fragment, and ligated to EcoRI-digested p498-4 plasmid to generate plasmid p498-6, where PD498 protease expression is driven by the cryIIIA promoter (FIG. 5). *B. subtilis* colonies containing the promoter in the correct orientation relative to the PD498 coding region are selected by their ability to form halos on agar plates containing the appropriate antibiotic and 1% milk.

6.2.1.8. Construction of vector Containing PD498 Protease Driven By The BAN Promoter The *Bacillus amyloliquefaciens* amylase (BAN) promoter is PCR-amplified from a plasmid (pSX222) (SEQ ID NO:23) using an upstream primer containing an additional SphI linker,
5'-GCATGCAATCGATTGTTTGAGAAAAGAAG-3', (SEQ ID NO:24)
where the first set of underlined nucleotide sequences is the said SphI site and the second set of underlined nucleotide sequences is a naturally occurring ClaI site; and a downstream primer,
5'-CATTTTCTTATACAAATTATATTTTACATATCAG-3' (SEQ ID NO:25).

The resulting 168 bp fragment is cloned into the pCRII vector (Invitrogen), removed as an EcoRI fragment, and ligated to EcoRI-digested p498-4 plasmid to generate plasmid p498-7, where PD498 protease expression is driven by the BAN promoter (FIG. 5). *B. subtilis* colonies containing the promoter in the correct orientation relative to the PD498 coding region are selected by their ability to form halos on agar plates containing the appropriate antibiotic and 1% milk.

*B. subtilis* transformants containing the BAN promoter in the reverse orientation relative to the PD498 protease are selected by their inability to form halos on agar plates containing the appropriate antibiotic and 1% milk.

6.2.2. Sequence Analysis of the PD498 Gene

Using two groups of oligonucleotides based on partial amino acid sequence of the PD498 protease, the correct sized fragment of 180 bp is amplified by PCR and cloned into the *E. coli* vector pCRII. Sequencing of the 180 bp insert reveals that the correct fragment is cloned. Using the 180 bp insert as a probe, Southern hybridizations identify a 6.5 kb EcoR1 fragment from PD498 chromosomal DNA that hybridize to the probe. Chromosomal DNA from PD498 is digested with EcoR1 and fragments of 5–8 kb are size-selected and ligated into pUC19 that is cut with EcoR1 and treated with CIP. Thousands of white colonies result after transformation into *E. coli* strain DH5α selecting on LB plates containing Amp and X-gal. 2 of 600 colonies screened are positive by colony hybridization using the labeled 180 bp fragment as a probe. Restriction analyses indicate that both colonies contain identical plasmids with a 6.5 kb EcoR1 insert.

DNA sequencing indicates that the 5' EcoR1 site is just upstream of the genes ribosome binding site (FIG. 3; SEQ ID NO:26) followed by the ATG initiation codon of the protein. The first 27 amino acids resemble a typical Bacillus signal peptide with a short sequence containing three positively charged residues followed by a hydrophobic stretch ending with Ser-Leu-Ala. After this cleavage site, there is a propeptide of 90 amino acids followed by the mature protein of 280 amino acids with a predicted molecular weight of 29270, which is in close agreement with the observed molecular weight of 34,000 (FIG. 4) on SDS-PAGE.

6.3. Isolation of a DNA Sequence Upstream of the PD498 Open Reading Frame With Promoter Activity DNA sequencing of the PD498 coding region indicates the presence of Asp718 (site also recognized by KpnI), PstI, BglII, and other unique restriction sites. Digestion of PD498 genomic DNA with Asp718 and a variety of other enzymes, Southern transfer of the fragments to nylon, and detection with the 180 bp DIG-labeled DNA probe (described in sections 6.2.1.3 and 6.2.1.4), indicates the presence of a 1.4 kb HindIII-Asp718 fragment. From the location of the known Asp718 restriction site in the PD498 coding region, the 1.4 kb HindIII-Asp718 fragment should contain approx 750–850 nts upstream of the ATG translational start of the PD498 protease. A size-selected library of 1–2 kb HindIII-Asp718 fragments is cloned into pUC118 (Vieira and Messing, Methods Enzymol. 153: 3–11, 1987) and transformed into *E. coli* XL1-Blue MRF' cells (Stratagene, San Diego, Calif.). Colonies are screened with the 180 bp DIG-labeled PCR fragment by the colony hybridization technique of Sambrook et al., 1989, supra. Six colonies are detected with the probe, and plasmid DNA is isolated from 4 colonies by the alkaline lysis technique (Sambrook et al., 1989, supra). All four plasmid preparations contain a 1.4 kb HindIII-Asp718 fragment. The sequence of this fragment is determined by Taq polymerase cycle-sequencing with fluorescent-labeled dideoxynucleotides on an ABI 373A sequencer (SEQ ID NO:4). The plasmid containing the fragment is termed p118-498prom1 (see FIG. 6).

6.4. Reconstruction of the PD498 Promoter with the PD498 Coding Sequence

The upstream HindIII-Asp718 fragment is reconstituted with its native PD498 coding sequence in three steps (see FIG. 9). First, the HindIII-Asp718 fragment from p118-498prom1 is cloned into pHP13amp. Then, plasmid p498-5 is digested with MscI and BamHI to yield a 1.0 kb MscI-BamHI fragment containing the coding region of the PD498 protease. Third, the MscI-BamHI fragment is ligated into the plasmid of step one cut with MscI and BamHI. The ligation mixture is then transformed into *E. coli* DH5α cells. The desired construct, p498-8 (see FIG. 9), is isolated from transformants by alkaline lysis "miniprepping". The plasmid is then transformed into a *B. subtilis* protease deficient strain and plated on TBAB plates containing 1% non-fat dry milk and 10 µg chloramphenicol per ml. Expression of the protease from its native promoter is indicated by the formation of clear zones (halos) around each transformed *B. subtilis* colony.

6.5. PD498

Shake flask experiments are performed in a sucrose/soybean flour medium with a *B. subtilis* protease deficient strain transformed with p498-5, 6, 7, 8, and "7R". These plasmid constructs consist of the pHP13amp vector containing the amyL, cryIIIA, BAN, 498, and reverse BAN (BAN promoter in reverse orientation) respectively, driving PD498 protease expression. *B. licheniformis* alpha-amylase under the control of cryIIIA, BAN, and PD498 promoters is produced after four days.

6.6. Lipolase Expression in *Bacillus subtilis*

The following contructs are tested in a *B. subtilis* protease deficient background: (promoter/signal sequence/Lipolase®)

|          | Lipolase® Activity |
|----------|--------------------|
| pHP13amp | 0                  |
| pLip3    | 5                  |

A diagram of pHP13amp is shown in FIG. 7 and a diagram of pLip3 is shown in FIG. 8. The following procedure is used to consruct pLip3. The MscI-BamHI fragment of pMHan37 (see FIG. 10), bearing the proLipolase®coding sequence, is ligated with the HindIII-MscI fragment of PD498 from p118-498prom1 (comprising the promoter and signal peptide coding sequence) and HindIII/BamHI-cut pHP13 amp to produce pLip3. A protease deficient *B. subtilis* strain is transformed with this consturct. When patched on TBAB plates containg 5 ug chloramphenicol/ml and 1% tributyrin, transformants make larger zones of clearing than the *B. subtilis* protease deficient strain contiang pHP13amp alone. A diagram of the fusion is shown in FIG. 11.

These results are obtained from shake flasks using a sucrose-soy media. The data show that the pD498 promoter/signal sequence can be used to express a heterologous protein in *B. subtilis*.

7. DEPOSIT OF MICROORGANISMS

The following biological materials have been deposited in the Agricultural Research Service Patent Culture Collection (NRRL), Northern Regional Research Center, 1815 University Street, Peoria, Ill., 61604, USA.

| Strain                              | Accession No. | Deposit Date   |
|-------------------------------------|---------------|----------------|
| *E. coli* containing p498-5         | NRRL B-21434  | April 24, 1995 |
| *E. coli* containing p118-498prom1  | NRRL B-21433  | April 24, 1995 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122 and under conditions of the Budapest Treaty. The deposit represents a biologically pure culture of each deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A nucleic acid construct comprising a nucleic acid sequence encoding an alkaline protease wherein said alkaline protease-encoding sequence comprises a region encoding a mature protease having the amino acid sequence of SEQ ID NO:8.

2. The nucleic acid construct of claim 1 wherein said coding sequence is endogenous to *Bacillus sp.* PD498.

3. The nucleic acid construct of claim 1 wherein said encoded mature protease has substantially all of the immunochemical properties as an alkaline protease endogenous to *Bacillus sp.* PD498.

4. A nucleic acid construct comprising the nucleic acid sequence set forth SEQ ID NO:1.

5. A nucleic acid construct comprising the nucleic acid sequence set forth in SEQ ID NO:3.

6. A nucleic acid construct comprising a nucleic acid sequence encoding an alkaline protease having the amino acid sequence of SEQ ID NO:4.

7. A nucleic acid construct comprising the nucleic acid sequence set forth in SEQ ID NO:5.

8. A nucleic acid construct comprising a nucleic acid sequence encoding an alkaline protease having the amino acid sequence of SEQ ID NO:6.

9. A nucleic acid construct comprising the nucleic acid sequence set forth in SEQ ID NO:7.

10. A recombinant host cell comprising the nucleic acid construct of claim 1.

11. The recombinant host cell comprising the nucleic acid construct of claim 4.

12. The recombinant host cell comprising the nucleic acid construct of claim 8.

13. The recombinant host cell comprising the nucleic acid construct of claim 5.

14. The recombinant host cell comprising the nucleic acid construct of claim 6.

15. A recombinant vector comprising (a) the nucleic acid construct of claim 1; (b) a promoter sequence operably linked to the nucleic acid sequence of (a); and (c) a selectable marker.

16. A recombinant vector comprising (a) the nucleic acid construct of claim 4; (b) a promoter sequence operably linked to the nucleic acid sequence of (a); and (c) a selectable marker.

17. A recombinant vector comprising (a) the nucleic acid construct of claim 8; (b) a promoter sequence operably linked to the nucleic acid sequence of (a); and (c) a selectable marker.

18. A recombinant vector comprising (a) the nucleic acid construct of claim 5; (b) a promoter sequence operably linked to the nucleic acid sequence of (a); and (c) a selectable marker.

19. A recombinant vector comprising (a) the nucleic acid construct of claim 6; (b) a promoter sequence operably linked to the nucleic acid sequence of (a); and (c) a selectable marker.

20. The recombinant vector of claim 15 in which the promoter sequence is selected from the group consisting of a cryIIIA promoter, a *Bacillus licheniformis* alpha-amylase promoter, a *Bacillus amyloliquifaciens* alpha-amylase promoter, and a promoter sequence comprising a transcriptional activating region of the nucleic acid sequence shown in SEQ ID NO:9.

21. The recombinant vector of claim 15 in which the vector further comprises a signal peptide-encoding nucleic acid sequence.

22. The recombinant vector of claim 21 in which said signal peptide-encoding nucleic acid sequence is selected from the group consisting of a *Bacillus licheniformis* alpha-amylase signal peptide-encoding nucleic acid, a *Bacillus amyloliquifaciens* alpha-amylase signal peptide-encoding nucleic acid, and a signal peptide-encoding nucleic acid sequence encoding the amino acid sequence set forth in SEQ ID NO:11.

23. A nucleic acid construct comprising a nucleic acid sequence encoding an alkaline protease endogenous to *Bacillus sp.* PD498, wherein said protease-encoding sequence hybridizes to a nucleotide sequence selected from the group of sequences consisting of SEQ ID NO:3, SEQ ID NO:5 and SEQ ID NO:7, said hybridization conducted for 18 hours at about 40° C. in 20% formamide, 50 mM sodium phophate pH6.8, and 50 g denatured sonicareal calf thymus DNA followed by a wash in 0.4XSSC at a temperature of about 45° C.

* * * * *